United States Patent [19]

Kindon et al.

[11] Patent Number: 5,985,849
[45] Date of Patent: Nov. 16, 1999

[54] PHOSPHATE COMPOUNDS AND THEIR USE AS MEDICAMENTS

[75] Inventors: Nicholas Kindon; Premji Meghani; Stephen Thom, all of Leics, United Kingdom

[73] Assignee: Astra Pharmaceuticals Ltd., Herts, United Kingdom

[21] Appl. No.: 09/068,076

[22] PCT Filed: Mar. 30, 1998

[86] PCT No.: PCT/SE98/00587

§ 371 Date: May 4, 1998

§ 102(e) Date: May 4, 1998

[87] PCT Pub. No.: WO98/45309

PCT Pub. Date: Oct. 15, 1998

[30] Foreign Application Priority Data

Apr. 4, 1997 [SE] Sweden .................................. 9701219

[51] Int. Cl.⁶ .................................................. A01N 43/04
[52] U.S. Cl. ........................ 514/51; 514/49; 514/50; 514/885; 536/26.26; 536/26.3; 536/26.8; 536/28.53; 536/28.54; 536/28.55
[58] Field of Search ........................ 536/26.26, 26.3, 536/26.8, 28.53, 28.54, 28.55; 514/49, 50, 51, 886

[56] References Cited

U.S. PATENT DOCUMENTS 5,627,165  5/1997  Glazier .

5,639,867  6/1997  Brill .

*Primary Examiner*—James O. Wilson
*Attorney, Agent, or Firm*—Nixon & Vanderhye

[57] ABSTRACT

A compound of the formula (I) or salts thereof:

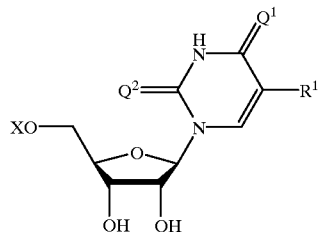

(I)

wherein X, $R^1$, $Q^1$ and $Q^2$ are as defined in the specification. The compounds have been found to be P2 7-TM G-protein receptor antagonists, especially to the P2 Y2 receptor, and are useful in therapy, for example as anti-inflammatory agents useful in the treatment of a number of inflammatory diseases such as asthma, inflammatory bowel disease, ARDS, psoriasis, rheumatoid arthritis, myocardial ischaemia, COPD, cystic fibrosis, arthrosclerosis, restenosis, peridontal disease, septic shock, osteoarthritis and stroke.

12 Claims, No Drawings

PHOSPHATE COMPOUNDS AND THEIR USE AS MEDICAMENTS

The invention provides new pharmaceutically active compounds, compositions containing them and processes for their preparation. The compounds are useful in therapy because they are P2-purinoceptor 7-transmembrane (TM) G-protein coupled receptor antagonists.

BACKGROUND OF THE INVENTION

ATP receptors have been shown to be present on a wide number of different cell types (Dubyak et al Am J Physiol (1993) 265, C577–C606). Neutrophils, monocytes and macrophages have been isolated from several species including humans and ATP and/or UTP have been shown to increase intracellular calcium levels. Activation of these receptors on leukocytes can either directly stimulate certain types of inflammatory response or can prime the effector cells to other inflammatory mediators in vivo. ATP can upregulate the expression of adhesion molecules (Freyer et al J Immun. (1988) 141, 580–586) which causes enhanced adhesion of circulating leukocytes to endothelial cells and their enhanced migration into the tissue space. ATP has also been shown to promote chemotaxis of both neutrophils and eosinophils (Verghese et al J. B. C. (1996) 271, 15597–15601 and Burders et al Blood (1993) 81, 49–55) which may promote an inflammatory response. ATP priming of neutrophils can also potentiate superoxide production (Seifert et al Eur J Biochem (1989) 181, 277–285). ATP receptors are also present on a number of other cell types such as chondrocytes, keratinocytes, microglia and goblet cells (Leong et al BBA (1994) 1201, 298–304; Pillai et al J Clin Invest (1992) 90, 42–51; Walz et al J Neuroscience (1993) 13, 4403–4411 and Abdullah et al Biochem J (1996) 316, 943–951). Stimulation of the receptors on these cells can stimulate or enhance inflammatory responses and antagonist of the receptor may therefore be of use in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. ATP receptors have also been reported on tumour cells (Dubyak et al J. Biol. Chem., (1985) 260, 10653–10661 and Wagner et al Gastroenterolgy, (1997), 112(4) suppl. page A1198) and may be involved in the development of cancer. Antagonists may therefore be useful in treatment of cancer.

DESCRIPTION OF THE INVENTION

According to the invention there is provided a compound of formula (I) or salts thereof:

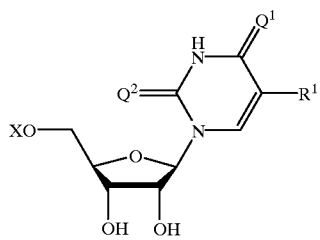

(I)

wherein X represents H or a group of formula (i), (ii) or (iii):

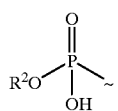

(i)

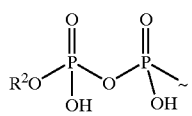

(ii)

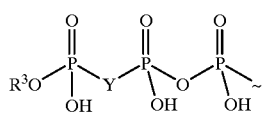

(iii)

$R^1$ represents a $C_{1-6}$-alkyl, $C(R^4)_2R^5$, $CHR^6R^5$, $Si(R^4)_3$, $C(O)R^6$, or $SR^6$ group or
$R^1$ represents a group of formula (iv) or (v):

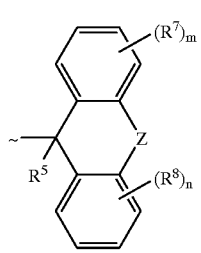

(iv)

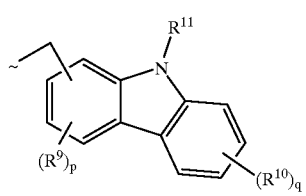

(v)

$R^2$ represents a hydrogen atom or methyl;
$R^3$ represents a hydrogen atom or a $C_{1-6}$-alkyl group which is optionally substituted by one or more $C_{1-6}$-alkoxy, $C_{1-6}$-alkylthio, $C_{3-8}$-cycloalkyl, and/or phenyl groups (wherein the one or more phenyl groups are optionally substituted by one or more halogen atoms and/or hydroxy, $C_{1-4}$-alkyl and/or $C_{1-4}$-alkoxy groups);
$R^4$ represents phenyl optionally substituted by one or more halogen atoms and/or one or more $C_{1-4}$-alkoxy, $C_{1-4}$-alkylthio and/or $C_{1-4}$-alkyl groups (wherein the one or more alkyl groups are optionally substituted by one or more F atoms);
$R^5$ represents a hydrogen atom or a $C_{1-6}$-alkoxy, $C_{1-6}$-alkylthio, $C_{1-6}$-alkyl or a phenyl group;
$R^6$ represents a $C_{6-10}$-aryl group which is optionally substituted by one or more halogen atoms and/or one or more $C_{6-10}$-aryl, $C_{6-10}$-aryloxy, $C_{6-10}$-arylthio, $C_{3-8}$-cycloalkyl, $C_{1-6}$-alkylthio, $C_{1-6}$-alkyl and/or $C_{1-6}$-alkoxy groups, each of which substituents are optionally substituted by one or more halogen atoms and/or one or more $C_{1-6}$-alkyl, phenyl and/or $C_{1-6}$-alkoxy groups;
$R^7$ and $R^8$ each independently represent a halogen atom or a $C_{1-4}$-alkoxy, $C_{1-4}$-alkylthio or $C_{1-4}$-alkyl group (wherein the one or more alkyl groups are optionally substituted by one or more F atoms);

$R^9$ and $R^{10}$ each independently represent a halogen atom or a $C_{1-4}$-alkoxy, $C_{1-4}$-alkylthio, $C_{1-4}$-alkyl (optionally substituted by a phenyl group) or a $C_{3-8}$-cycloalkyl group;

$R^{11}$ represents $C_{1-6}$-alkyl group optionally substituted by phenyl;

$Q^1$ and $Q^2$ each independently represent O or S;

Y represents O or a $CF_2$, $CCl_2$ or a $CBr_2$ moiety;

Z represents a direct bond, O, S, $(CH_2)_t$ (wherein when t is greater than 1, one of the $CH_2$ moieties is optionally replaced by an O or S atom), $CH_2CH=CH$, $CH_2CH=CHCH_2$ or $CH=CH$;

n, m, p and q each independently represent 0 or an integer from 1 to 4;

t represents an integer from 1 to 4;

provided that:
(a) when X represents H then Q represents a S atom and $R^1$ represents a group of formula (iv) where $R^5$ is hydrogen, and Z is $CH_2CH_2$ or $CH=CH$;
(b) when $R^3$ represents H then Y does not represent O;
(c) when X represents a group of formula (i) or (ii) then:
  (i) $R^1$ represents a group of formula (iv) wherein Z represents a direct bond, O, $CH=CH$, or $CH_2CH_2$, and $R^7$, $R^8$, n and m are as defined above; or
  (ii) $R^1$ represents $C(R^4)_2R^5$ wherein $R^4$ represents phenyl substituted by one or more halogen atoms and/or one or more $C_{1-4}$-alkoxy, $C_{1-4}$-alkylthio and/or $C_{1-4}$-alkyl groups (wherein the one or more alkyl groups are optionally substituted by one or more F atoms) and $R^5$ represents a hydrogen atom; or
  (iii) $R^1$ represents $CHR^6R^5$ wherein $R^6$ represents a $C_{6-10}$-aryl group which is substituted by one or more halogen atoms and/or one or more $C_{6-10}$-aryl, $C_{6-10}$-aryloxy, $C_{6-10}$-arylthio, $C_{3-8}$-cycloalkyl, $C_{1-6}$-alkylthio, $C_{1-6}$-alkyl and/or $C_{1-6}$-alkoxy groups, each of which optional substituents are optionally substituted by one or more halogen atoms and/or one or more $C_{1-6}$-alkyl, phenyl and/or $C_{1-6}$-alkoxy groups and $R^5$ is as defined above but does not represent phenyl;
(d) when $R^1$ represents $C_{1-6}$-alkyl then $Q^1$ represents a S atom;
(e) when $R^1$ represents $CHR^5R^6$ then $R^5$ does not represent phenyl.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

As used herein the term alkyl group, including the alkyl portion of alkoxy and alkylthio groups, includes straight or branched chain alkyl groups. Heterocyclyl or cycloalkyl groups include those comprising of more than one ring having one or two ring atoms in common. Aryl groups include fused ring systems for example naphthyl, as well as phenyl groups.

Preferably the compound of the invention forms a pharmaceutically acceptable salt, especially with an alkali metal, an alkaline earth metal and/or $N(R^{12})_4$ wherein each $R^{12}$ represents H or a $C_{1-6}$-alkyl group, for example n-butyl. Suitable alkali metals include Li, Na or K; suitable alkaline earth metals include Mg or Ca.

Preferably X represents a group of formula (iii) where Y represents a $CF_2$, $CCl_2$ or a $CBr_2$ moiety, more preferably a $CCl_2$ moiety and $R^3$ represents a hydrogen atom.

Preferably $R^1$ represents $C(R^4)_2R^5$ or a group of formula (iv).

Preferably $R^4$ represents phenyl which is substituted by one or more halogen atoms (preferably chlorine) and/or one or more methyl groups; more preferably it is substituted in the 4-position.

Preferably $R^5$, $R^7$ and $R^8$ each represent hydrogen, methyl, chloro or trifluoromethyl. More preferably $R^5$, $R^7$ and $R^8$ each represent hydrogen.

Preferably $Q^1$ represents a sulphur atom and $Q^2$ represents an oxygen atom.

Preferably Z represents a direct bond, O, $(CH_2)_2$ or $CH=CH$, more preferably $CH=CH$.

Particularly preferred compounds according to the invention include:

monoanhydride of 5-diphenylmethyluridine-5'-phosphate with dichloromethylenebisphosphonic acid;

monoanhydride of 5-(9H-fluoren-9-yl)-4-thiouridine-5'-phosphate with dichloromethylenebisphosphonic acid;

monoanhydride of 5-(9H-xanthen-9-yl)-4-thiouridine-5'-phosphate with dichloromethylenebisphosphonic acid;

monoanhydride of 5-(5H-dibenzo[a,d]cyclohepten-5-yl)-4-thiouridine-5'-phosphate with dichloromethylenebisphosphonic acid;

5-(5H-Dibenzo[a,d]cyclohepten-5-yl)-4-thiouridine;

monoanhydride of 5-(10,11-dihydro-5H-dibenzo[a,d] cyclohepten-5-yl)-4-thiouridine-5'-phosphate with dichloromethylenebisphosphonic acid;

5-(10,11-dihydro-5H-dibenzo[a,d]cyclohepten-5-yl)-4-thiouridine;

monoanhydride of 5-(1,1-bis(4-methylphenyl)methyl)-4-thiouridine-5'-phosphate with dichloromethylenebisphosphonic acid;

monoanhydride of 5-(1,1-bis(4-chlorophenyl)methyl)-4-thiouridine-5'-phosphate with dichloromethylenebisphosphonic acid;

monoanhydride of 5-(1,1-bis(3,4-dichlorophenyl)methyl)-4-thiouridine-5'-phosphate with dichloromethylenebisphosphonic acid;

monoanhydride of 5-(1,1-bis(4-methoxyphenyl)methyl)-4-thiouridine-5'-phosphate with dichloromethylenebisphosphonic acid;

monoanhydride of 5-(3,6-dimethoxy-9H-fluoren-9-yl)-4-thiouridine-5'-phosphate with dichloromethylenebisphosphonic acid;

monoanhydride of 5-(3-(4-methylphenoxy)phenylmethyl)-4-thiouridine-5'-phosphate with dichloromethylenebisphosphonic acid;

monohydride of 5-(3-(4-chlorophenoxy)phenylmethyl)-4-thiouridine-5'-phosphate with dichloromethylenebisphosphonic acid;

monoanhydride of 5-(3-(3,4-dichlorophenoxy) phenylmethyl)-4-thiouridine-5'-phosphate with dichloromethylenebisphosphonic acid;

monoanhydride of 5-(3-(4-methoxyphenoxy) phenylmethyl)-4-thiouridine-5'-phosphate with dichloromethylenebisphosphonic acid;

monoanhydride of 5-((3-methoxy-4-phenylmethoxy) phenylmethyl)-4-thiouridine-5'-phosphate with dichloromethylenebisphosphonic acid;

monoanhydride of 5-((4-methoxy-3-phenylmethoxy) phenylmethyl)-4-thiouridine-5'-phosphate with dichloromethylenebisphosphonic acid;

monoanhydride of 5-(4-butoxyphenylmethyl)-4-thiouridine-5'-phosphate with dichloromethylenebisphosphonic acid;

monoanhydride of 5-(9-ethylcarbazol-3-ylmethyl)-4-thiouridine-5'-phosphate with dichloromethylenebisphosphonic acid;

monoanhydride of 5-((4-phenyl)phenylthio)-4-thiouridine-5'-phosphate with dichloromethylenebisphosphonic acid;

monoanhydride of 5-(9-methoxyfluoren-9-yl)uridine-5'-phosphate with dichloromethylenebisphosphonic acid;

monoanhydride of 5-((4-phenyl)phenylcarbonyl)uridine-5'-phosphate, monoanhydride with dichloromethylenebisphosphonic acid;

5-diphenylmethyluridine-5'-(tetrahydrogen-triphosphate)-$P^3$-monomethyl ester;

5-diphenylmethyluridine-5'-(tetrahydrogen-triphosphate)-$P^3$-mono(n-propyl)ester;

5-diphenylmethyluridine-5'-(tetrahydrogen-triphosphate)-$P^3$-mono(2-methoxyethyl)ester;

5-diphenylmethyluridine-5'-(tetrahydrogen-triphosphate)-$P^3$-monophenylmethyl ester;

5-diphenylmethyl-4-thiouridine-5'-(tetrahydrogen-triphosphate)-$P^3$-monomethyl ester;

5-(1,1-bis(4-phenylmethyl)methyl)uridine-5'-(tetrahydrogen-triphosphate)-$P^3$-monomethyl ester;

5-(1,1-bis(4-methoxyphenyl)methyl)-4-thiouridine-5'-(tetrahydrogen triphosphate)-$P^3$-monomethyl ester;

5-(1,1-bis(4-methoxyphenyl)methyl)-4-thiouridine-5'-(dihydrogen-phosphate)-monomethyl ester;

5-(9H-fluoren-9-yl)uridine-5'-(tetrahydrogen-triphosphate)-$P^3$-monomethyl ester;

5-(9H-fluoren-9-yl)-4-thiouridine-5'-(tetrahydrogen-triphosphate)-$P^3$-monomethyl ester;

5-(9H-fluoren-9-yl)-4-thiouridine-5'-(trihydrogen-diphosphate)-$P^3$-monomethyl ester;

5-(9H-fluoren-9-yl)-4-thiouridine-5'-(dihydrogen-phosphate)-monomethyl ester;

5-triphenylsilyluridine-5'-(tetrahydrogen-triphosphate)-$P^3$-monomethyl ester;

5-phenylthiouridine-5'-(tetrahydrogen-triphosphate)-$P^3$-monomethyl ester;

5-ethyl-4-thiouridine-5'-(tetrahydrogen-triphosphate)-$P^3$-monomethyl ester;

5-((4-methoxy)phenylthio)uridine-5'-(tetrahydrogen triphosphate)-$P^3$-monomethyl ester;

5-((2-phenyl)phenylthio)uridine-5'-(tetrahydrogen-triphosphate)-$P^3$-monomethyl ester;

5-((3-phenyl)phenylthio)uridine-5'-(tetrahydrogen-triphosphate)-$P^3$-monomethyl ester;

5-((4-phenyl)phenylthio)uridine-5'-(tetrahydrogen-triphosphate)-$P^3$-monomethyl ester;

5-(2-naphthylthio)uridine-5'-(tetrahydrogen-triphosphate)-$P^3$-monomethyl ester;

5-((3-phenoxy)phenylmethyl)-4-thiouridine-5'-(tetrahydrogen-triphosphate)-$P^3$-monomethyl ester;

5-((4-phenoxy)phenylmethyl)-4-thiouridine-5'-(tetrahydrogen-triphosphate)-$P^3$-monomethyl ester;

5-((3-phenylmethoxy)phenylmethyl)-4-thiouridine-5'-(tetrahydrogen-triphosphate)-$P^3$-monomethyl ester;

5-((4-phenylmethoxy)phenylmethyl)-4-thiouridine-5'-(tetrahydrogen-triphosphate)-$P^3$-monomethyl ester;

5-(4-(1,1-dimethylethyl)phenylmethyl)-4-thiouridine-5'-(tetrahydrogen-triphosphate)-$P^3$-monomethyl ester;

5-(4-(1,1-dimethylethyl)phenylmethyl)-4-thiouridine-5'-(dihydrogen-phosphate)-monomethyl ester;

5-((3-methoxy-4-phenylmethoxy)phenylmethyl)-4-thiouridine-5'-(tetrahydrogen-triphosphate)-$P^3$-monomethyl ester; or 5-((3-methoxy-4-phenylmethyloxy)phenylmethyl)-4-thiouridine-5'-(trihydrogen-diphosphate)-$P^2$-monomethyl ester; or a salt thereof.

Especially preferred compounds of the invention include:

monoanhydride of 5-(9H-fluoren-9-yl)-4-thiouridine-5'-phosphate with dichloromethylenebisphosphonic acid;

monoanhydride of 5-(9H-xanthen-9-yl)-4-thiouridine-5'-phosphate with dichloromethylenebisphosphonic acid;

monoanhydride of 5-(5H-dibenzo[a,d]cyclohepten-5-yl)-4-thiouridine-5'-phosphate with dichloromethylenebisphosphonic acid;

monoanhydride of 5-(10,11-dihydro-5H-dibenzo[a,d]cyclohepten-5-yl)-4-thiouridine-5'-phosphate with dichloromethylenebisphosphonic acid;

monoanhydride of 5-(1,1-bis(4-methylphenyl)methyl)-4-thiouridine-5'-phosphate with dichloromethylenebisphosphonic acid; or monoanhydride of 5-(1,1-bis(4-chlorophenyl)methyl)-4-thiouridine-5'-phosphate with dichloromethylenebisphosphonic acid; or salts thereof.

More especially preferred compounds of the invention are:

monoanhydride of 5-(5H-dibenzo[a,d]cyclohepten-5-yl)-4-thiouridine-5'-phosphate with dichloromethylenebisphosphonic acid; or monoanhydride of 5-(10,11-dihydro-5H-dibenzo[a,d]cyclohepten-5-yl)-4-thiouridine-5'-phosphate with dichloromethylenebisphosphonic acid; or salts thereof.

According to a further aspect of the invention there is provided a process for the preparation of a compound of formula I, or a salt thereof, which comprises (a) for a compound of formula (I) wherein X represents H, deprotecting a compound of formula

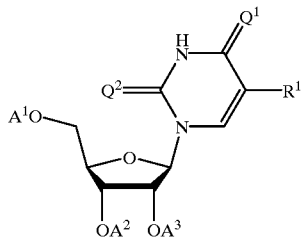

(II)

wherein $R^1$, $Q^1$ and $Q^2$ are as defined above and $A^1$, $A^2$ and $A^3$ each independently represent a protecting group;

(b) for a compound of formula (I) wherein X represents

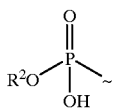

wherein $R^2$ is as defined above, reacting the product of step (a) with a phosphorylating agent $P(O)L_3$ wherein each L is the same or different and represents a leaving group, to yield an intermediate of formula (III)

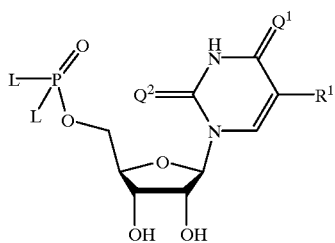

wherein L, $Q^1$, $Q^2$ and $R^1$ are as defined above, and either hydrolysing the intermediate of formula (III) thus obtained under alkaline conditions or reacting it with MeOH followed by alkaline hydrolysis;

(c) for a compound of formula (I) wherein X represents

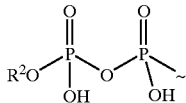

wherein $R^2$ is as defined above, hydrolysing an intermediate of formula (III) as defined above and then reacting it with a phosphorylating agent $P(O)L_3$ as defined above, and either hydrolysing the product under alkaline conditions or reacting it with MeOH followed to by alkaline hydrolysis:

(d) for a compound of formula (I) wherein X represents

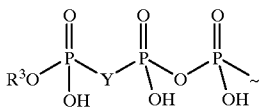

wherein $R^3$ represents H and Y is as defined above, reacting an intermediate of formula (III) as defined above with a salt of a compound of formula (IV)

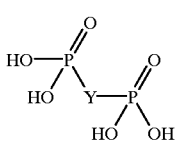

wherein Y is as defined above followed by alkaline hydrolysis; or (e) for a compound of formula (I) wherein X represents

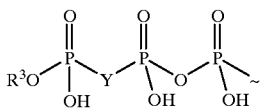

wherein $R^3$ is as defined for the compound of formula (I) but does not represent H and Y is as defined above, reacting the product of step (d) with a phosphorylating agent $P(O)L_3$ as defined above, and reacting the product with $R^3OH$ wherein $R^3$ is as defined above; and, optionally (f) forming a salt.

A compound of formula (I) wherein X represents:

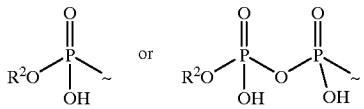

wherein $R^2$ is as defined above may also be obtained as by-products from step (e).

The invention further provides an intermediate of formula (II) wherein its substituents are as defined above, provided that $R^1$ does not represent $C_{1-6}$-alkyl, $C(O)R^6$, $CHR^5R^6$ or $SR^6$ wherein $R^6$ represents unsubstituted phenyl and $R^5$ does not represent a H atom. $A^1$, $A^2$ and $A^3$ preferably represent $(C_{1-6}$-alkyl$)_3$Si (especially t-butyldimethylsilyl), wherein the silyl groups represented by $A^1$ and $A^2$ are optionally connected via an O atom so as to complete a ring.

The deprotection reaction in step (a) of the process of the invention may be carried out using methods generally known in the art (see "Protective Groups in Organic Chemistry" by Theodora Greene, John Wiley and Sons Inc., 1981). Step (a) is preferably carried out using, for example, a fluoride ion source, for example tetra-n-butylammonium fluoride or a hydrogen fluoride/pyridine complex, or caesium fluoride, in a suitable aprotic solvent, such as tetrahydrofuran, acetonitrile, diethylether or dichloromethane.

In steps (b) and (c), the phosphorylating agent is preferably one where L represents halogen, more preferably chlorine. In step (e), the phosphorylating agent is preferably one where L represents halogen (more preferably chlorine) or O-phenyl; most preferably the agent is $P(O)(OPh)_2Cl$.

The reaction in steps (b) and (c) with a phosphorylating agent is preferably carried out in the presence of a base, such as 1,8-bis(dimethylamino)naphthalene, and/or an inert base such as a tri-$C_{1-8}$-alkylamine, for example triethylamine, tri-n-butylamine, N,N-diethylisopropylamine or tri-n-octylamine. The reaction is preferably carried out in a solvent, preferably a dipolar aprotic solvent, for example, trimethylphosphate, triethylphosphate, acetonitrile, and preferably at a temperature of from −20 to 20° C. more preferably from −5° C. to 5° C.

In steps (b), (c) and (d), the compound of formula (III) is preferably not isolated but is reacted in situ. Similarly in step (e) the product of step (d) is preferably not isolated but reacted in situ.

In step (d) where Y in the compound of formula (IV) does not represent O, the reaction time is preferably from 2 to 8 hours and the reaction temperature is preferably from 0 to 40° C., more preferably from 0 to 25° C. The alkaline hydrolysis step is carried out for 5 to 48 hours.

In step (d) where Y in the compound of formula (IV) represents O, the reaction time is preferably from 2 to 10 minutes (more preferably about 5 minutes) and the reaction temperature is preferably from −5 to 5° C., more preferably about 0° C.

In step (e) the phosphorylation reaction time is preferably from 1 to 5 hours (more preferably about 2.5 hours) in a suitable aprotic solvent (preferably 1,4-dioxane) preferably at a temperature of from 10 to 40° C. (more preferably about 25° C.). The resulting intermediate is reacted with $R^3OH$ in a suitable solvent (preferably pyridine) for preferably from 1 to 5 hours (more preferably about 2.5 hours).

The salt of the compound of formula (IV) as defined above used in step (d) is preferably the mono tri-n-butylammonium salt.

In steps (b), (c) and (d), hydrolysis is preferably a base-catalysed hydrolysis; for example using aqueous triethyl ammonium bicarbonate, $Na_2CO_3$, $NaHCO_3$, $K_2CO_3$, $KHCO_3$, or any alkaline earth metal carbonate salt.

Salts of the compounds of formula (I) may be formed by reacting the free acid, or a salt thereof, with one or more equivalents of the appropriate base (for example ammonium hydroxide optionally substituted by $C_{1-6}$-alkyl or an alkali metal or alkaline earth metal hydroxide). The reaction may be carried out in a solvent or medium in which the salt is insoluble or in a solvent in which the salt is soluble, e.g. water, alcohol or acetone, which may be removed in vacuo, or by freeze drying. The reaction may also be a metathetical process or it may preferably be carried out on an ion exchange resin. The non-toxic physiologically acceptable salts are preferred, although other salts may be useful, e.g. in isolating or purifying the product.

A compound of formula (II) wherein $Q^1$ and/or $Q^2$ represent S may be synthesised from a compound of formula (II) wherein $Q^1$ and $Q^2$ represent O using standard thiation conditions for conversion of uridine and thymidine nucleosides into their corresponding thio-nucleoside derivatives (see "Chemistry of Nucleosides and Nucleotides" edited by Leroy B. Townsend, Plenum Press volume 1). For example conditions such as phosphorus pentasulphide or Lawesson's reagent in inert solvent(s) such as pyridine, toluene, xylene, tetrahydrofuran, and/or 1,4-dioxane at temperatures of from 50° C. to 130° C. could be used.

Compounds of formula (II) may be synthesised directly (using the procedure described in Tetrahedron Letters, 1987, 28 (1), 87–90 or a modified procedure thereof) by metallation of the protected uridine of formula

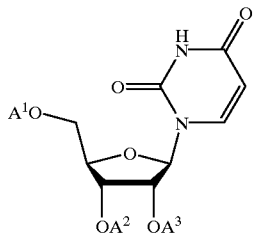

(V)

wherein $A^1$, $A^2$ and $A^3$ are as defined above, using for example alkylmetallic reagents such as n-butyllithium, sec-butyllithium, tert-butyllithium or metallic dialkylamides such as lithium diisopropylamide, lithium-, sodium- or potassium-hexamethyldisilazane, in the absence or presence (preferably presence) of metal chelating agents such as N,N,N'N'-tetramethylenediamine, hexamethylphosphoramide. Preferably sec-butyl lithium with N,N,N'N'-tetramethylenediamine are used. Metallation is followed by reacting the intermediate organometallic species with an electrophile such as $(C_{1-5}$-alkyl$)$-CHO, $R^4C(O)R^4$, $R^6CHO$, $R^6SSR^6$, $R^6COHal$, $(R^4)_3SiHal$, $R^6CH_2Hal$, $(C_{1-6}$-alkyl$)$-Hal or

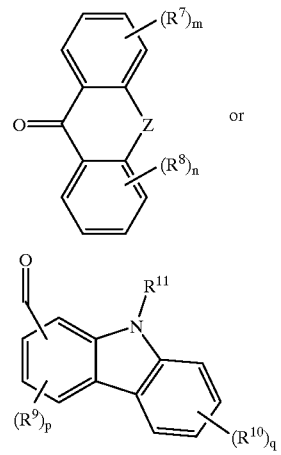

wherein Z, $R^4$, $R^6$, $R^7$, $R^8$, $R^9$, $R^{10}$, $R^{11}$, n, m, p and q are as defined above and Hal represents a halogen atom, preferably bromine or iodine. The metallation is generally carried out at low temperatures, for example from −40° C. to −78° C., and in dried solvents, for example tetrahydofuran, diethylether, glyme and/or diglyme, under a inert atmosphere, for example under nitrogen or argon gas.

Where the electrophile was an aldehyde or a ketone and $R^5$ represents a hydrogen atom, the metallation is followed by reduction using standard reducing conditions suitable to remove a hydroxyl group. For example the reducing agents may be hydrogen gas in the presence of a catalyst, such as platinum, platinum oxide, palladium, palladium oxide, Raney Nickel or rhodium, on a support, such as charcoal, using an alcohol, such as ethanol, or an ester, such as ethyl acetate, as the reaction solvent, or a mixture of solvents, at normal or elevated pressure. The preferred temperature is room temperature. The preferred pressure is from 1 to 3 atmospheres. The preferred reducing agent is triethylsilane, in the presence of a strong acid, such as trifluoroacetic acid, or a Lewis acid, such as a boron trifluoride ethyl etherate complex in a suitable inert solvent, such as dichloromethane, chloroform, 1,2-dichloroethane. Alternatively the reduction may be performed by electrons generated in situ by dissolving a suitable metal, for example iron, zinc, tin or magnesium, in a suitable acid, for example acetic acid, formic acid, dilute hydrochloric acid, dilute sulphuric acid, for example at a temperature of from 20 to 120° C.

Where the electrophile was an aldehyde or a ketone and $R^5$ does not represent a hydrogen atom, the metallation is followed by:

(i) where $R^5$ represents $C_{1-6}$-alkoxy reaction with a $C_{1-6}$-alkyl alcohol using the method of S Kim, K N Chung and S Yang JOC, 1987, 52, 3917–3919;

(ii) where $R^5$ represents $C_{1-6}$-alkylthio, reaction with a $C_{1-6}$-alkyl thioalcohol in the presence of $ZnI_2$ (Y Guindon, R Frenette, R Fortin, J Rokach, JOC, 1983, 48, 1357–1359);

(iii) where $R^5$ represents $C_{1-6}$-alkyl or a phenyl group, reaction with a suitable chlorinating agent such as trimethylsilyl chloride (Nucleosides and Nucleotides, 1993, vol 12, issues 3 & 4, pp 305–321) or thionyl chloride with pyridine, followed by reaction with the appropriate trialkyl or triphenyl thallide (I E Markó, M L Kantam, T Lett, 1991, 32, 2255–2258).

Compounds of formula (II) wherein $R^1$ represents $SR^6$ wherein $R^6$ is as defined above, can also be synthesised directly from 5-mercuriuridine using a compound of formula $R^4SSR^4$ and palladium tetrachloride using the method described in Journal of Organic Chemistry 1991, 56, (19), 5598 or a modified procedure thereof.

The compounds of the invention have been submitted to the assay outlined in Example A and have been found to be P2 7-TM G-protein receptor antagonists, particularly to the P2Y2 receptor. Accordingly they are useful in therapy and are, in particular, indicated for use as anti-inflammatory agents useful in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. ATP receptors have also been reported on tumour cells and may be involved in the development of cancer. Antagonists may therefore be useful in treatment of cancer.

The invention provides in a further aspect a method of treating an inflammatory condition which comprises administering to a patient in need of therapy, a therapeutically effective amount of a compound of the invention. The compounds of the invention can be co-administered with other anti-inflammatory agents.

According to the invention there is further provided use of the compounds of the invention in the manufacture of a medicament for use in the treatment of an inflammatory condition.

The compounds may be administered orally, topically e.g. to the lung and/or the airways, in the form of solutions, suspensions, HFA aerosols and dry powder formulations, e.g. Turbuhaler® formulations or by parenteral administration in the form of sterile parenteral solutions or suspensions.

The invention further provides a pharmaceutical composition comprising a compound according to the present invention in association with a pharmaceutically acceptable excipient and/or adjuvant. Particularly preferred are compositions not containing material capable of causing an adverse, e.g. an allergic, reaction. For example a chelating or sequestering agent, an antioxidant, a tonicity adjusting agent, a pH modifying agent and/or a buffering agent are suitable additives.

The compounds of the invention may also be administered by means of a dry powder inhaler. The inhaler may be a single or a multi dose inhaler, and may be a breath actuated dry powder inhaler.

A pharmaceutical composition according to the present invention could optionally be prepared in freeze dried form using any lyophilisation techniques commonly used within the pharmaceutical area. Upon use but before administration, such pharmaceutical compositions are generally reconstituted in a pharmaceutically acceptable excipient. Preferably a solution of the pharmaceutical composition according to the invention obtained after reconstitution is an isotonic solution. Such a pharmaceutical composition according to the present invention when reconstituted is preferably administered by injection, for example intravenously, subcutaneously or intramuscularly.

EXAMPLES

The invention is illustrated by the following examples which should not be interpreted as limiting the invention. In the examples the NMR spectra were measured on a Varian Unity Inova 300 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica; chromatography was generally performed using Matrex Silica 60® (35–70 micron) or Prolabo Silica gel 60® (35–75 micron) suitable for flash silica gel chromatography.

Example 1

Trisodium salt of the monoanhydride of 5-diphenylmethyluridine-5'-phosphate with dichloromethylenebisphosphonic acid (i) To a solution of 2',3',5'-tris-O-((1,1-dimethylethyl) dimethylsilyl)uridine (12 g) in dry tetrahydrofuran (300 ml) at −78° C. under a nitrogen atmosphere was added N,N,N', N'-tetramethylenediamine (6.8 ml) followed by sec-butyllithium (35 ml) (1.3M in cyclohexane) dropwise over 10 minutes. After 1 hour the reaction was quenched with a solution of benzophenone (7.5 g) dissolved in dry tetrahydrofuran (40 ml). After a further 1 hour the cooling bath was removed and the mixture was allowed to warm to approximately −10° C. before quenching with water (50 ml). The reaction mixture was extracted with dichloromethane (200 ml) three times and the organic extracts were pooled, dried over magnesium sulphate and evaporated to dryness to leave a pale yellow oil. The product was purified by silica-gel chromatography eluting with iso-hexane and ethyl acetate mixtures to give 5-(hydroxy-(1,1-diphenyl)methyl)-2',3',5'-tris-O-((1,1-dimethylethyl)dimethylsilyl)uridine as a colourless foam (9.0 g).

MS: FAB: (+Rb): m/e 853/5 (M+Rb)$^+$.

(ii) The product of step (i) (8.9 g) was dissolved in dichloromethane (100 ml) and triethylsilane (2 ml). Trifluoroacetic acid (8.9 ml) was added dropwise over 5 minutes and the mixture was stirred for a further 20 minutes. The volatiles were removed under reduced pressure and any residual traces were removed by addition of toluene (50 ml) and evaporation under reduced pressure (three times). The residual gum was treated with tetra-n-butylammonium fluoride (35 ml of a 1M solution in tetrahydrofuran) for 1 hour at room temperature. The volatiles were removed under reduced pressure and the gummy residue purified by silica-gel chromatography eluting with chloroform-methanol mixtures to give 5-diphenylmethyluridine as a white solid (4 g).

MS: FAB(+ve): m/e 411 (M+1)$^+$.

(iii) The product of step (ii) (0.44 g) and 1,8-bis(dimethylamino)naphthalene (0.37 g) were dissolved in dry triethylphosphate (5 ml) and then cooled to 0° C. under a nitrogen atmosphere. Phosphorous oxychloride (0.16 ml) was added dropwise and the resulting mixture stirred at 0° C. for 3 hours before addition of a pre-formed solution of the mono tri-n-butylammonium salt of dichloromethylenebisphosphonic acid (1.16 g) (Blackburn et al, J Chem Soc Chem Commun, 1981, 22, 1188–1190) with tri-n-butylamine (0.64 ml) in triethylphosphate (8 ml). After 5 minutes the mixture was allowed to reach room temperature by removing the cooling bath. After 4 hours the mixture was quenched by addition of aqueous sodium bicarbonate (2.5 g) solution (50 ml) and then stirred for a further 24 hours. The mixture was extracted twice with diethyl ether (50 ml). The aqueous phase was concentrated under reduced pressure and the residue purified by ion-exchange chromatography (DEAE Sephadex eluting with 0–0.5M triethylammonium bicarbonate solution). Fractions containing product were pooled, lyophilised and the residue was dissolved in water and passed down an ion-exchange column (Dowex-50 Na⁺ form). The UV (254 nm) active fractions were pooled and lyophilised and the residue was purified by reverse phase chromatography (C18 Sep-pak silica) eluting with water. Fractions containing the product were pooled and lyophilised to leave the trisodium salt of the monoanhydride of 5-diphenylmethyluridine-5'-phosphate with dichloromethylenebisphosphonic acid as a white powder (0.137 g).

$^{31}$ P NMR δ (D$_2$O): 8.94(d), 0.65(dd), −9.55(d).

MS: FAB (+ve): m/e 783 (M+1)⁺.

Example 2

Triammonium salt of the monoanhydride of 5-(9H-fluoren-9-yl)-4-thiouridine-5'-phosphate with dichloromethylenebisphosphonic acid (i) 5-(9-Hydroxyfluoren-9-yl)-2',3',5'-tris-O-(1,1-dimethylethyl)dimethylsilyl)uridine was prepared from 2',3',5'-tris-O-(1,1-dimethylethyl)dimethylsilyl)uridine according to the method of Example 1 step (i) (using 9-fluorenone instead of benzophenone) as a colourless foam.

MS: FAB(+Rb): m/e: 854/852 (M+Rb).

(ii) The product of step (i) (10.26 g) was dissolved in dichloromethane (200 ml) and triethylsilane (2.34 ml) and cooled to 0° C. before treating with boron trifluoride diethyletherate (3.3 ml) dropwise. After 30 minutes, the reaction was quenched with aqueous sodium bicarbonate (12 g in 300 ml of water). The organic phase was collected and dried over magnesium sulphate and the solvent was evaporated under reduced pressure. The residue was dissolved in dry dimethylformamide (40 ml) and treated with imidazole (1.82 g) and t-butyldimethylsilylchloride (2.02 g). After stirring for 16 hours, the mixture was quenched with water (100 ml) and the product was extracted into iso-hexane. The solvent was removed under reduced pressure and the residue which was 5-(9H-fluoren-9-yl)-2',3',5'-tris-O-(1,1-dimethylethyl) dimethylsilyl)uridine (8.05 g) was used directly in the next step.

(iii) The product of step (ii) (8.05 g) was dissolved in dry pyridine (200 ml) under a nitrogen atmosphere and treated with phosphorus pentasulphide (11.89 g) before refluxing for 16 hours. After cooling to room temperature, the solvent was evaporated under reduced pressure and the residue was quenched with saturated aqueous sodium bicarbonate solution followed by extraction of the product into ethyl acetate (three times). The combined extracts were dried over magnesium sulphate and the solvent was removed under reduced pressure. The remaining residue was purified by silica-gel chromatography eluting with iso-hexane/ethyl acetate mixtures to give 5-(9H-fluoren-9-yl)-2',3',5'-tris-O-(1,1-dimethylethyl)dimethylsilyl)-4-thiouridine as a yellow foam (5.50 g).

MS: FAB(−ve): 765(M−1).

(iv) The product of step (iii) (5.5 g) was treated with tetra-n-butyl ammonium fluoride (6.19 g) in tetrahydrofuran (24 ml) and the mixture stirred at room temperature for 3 hours. The solvent was evaporated under reduced pressure and the residue was purified by flash chromatography on silica-gel eluting with 10% methanol in ethyl acetate to give 5-(9H-fluoren-9-yl)-4-thiouridine as a pale yellow solid (3.43 g).

MS: EI: 424(M⁺)

(v) The triammonium salt of the monoanhydride of 5-(9H-fluoren-9-yl)-4-thiouridine-5'-phosphate with dichloromethylenebisphosphonic acid was prepared from the product of step (iv) according to the method of Example 1 step (iii) (with further purification by reverse phase HPLC using 10% methanol in 0.5% aqueous ammonium acetate) as a yellow powder.

$^{31}$ P NMR δ (D$_2$O): 8.68(d), 0.18(dd), −9.9(d).

MS: FAB (−ve): m/e 729/731/733 (M−1).

Example 3

Tetrasodium salt of the monoanhydride of 5-(9H-xanthen-9-yl)-4-thiouridine-5'-phosphate with dichloromethylenebisphosphonic acid (i) 5-(9-Hydroxyxanthen-9-yl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using xanthone instead of benzophenone) as a pale yellow solid.

MS: FAB(−ve): 781(M−1).

(ii) 5-(9H-Xanthen-9-yl)-2',3',5'-tris-O-((1,1-dimethylethyl)dimethylsilyl)uridine was prepared from the product of step (i) according to the method of Example 2 step (ii) as a pale yellow foam.

MS: FAB(−ve): 765(M−1).

(iii) 5-(9H-Xanthen-9-yl)-2',3',5'-tris-O-((1,1-dimethylethyl)dimethylsilyl)-4-thiouridine was prepared from the product of step (ii) according to the method of Example 2 step (iii) as a yellow solid.

MS: FAB(−ve): 781(M−1).

(iv) 5-(9H-Xanthen-9-yl)-4-thiouridine was prepared from the product of step (iii) according to the method of Example 2 step (iv) as a light-sensitive yellow solid.

MS: FAB(+ve): 441(M+1).

(v) The tetrasodium salt of the monoanhydride of 5-(9H-xanthen-9-yl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.44(d), 3.45(dd), −9.78(d).

MS: FAB (+ve): m/e 835/837/839 (M+1).

Example 4

The tetrasodium salt of the monoanhydride of 5-(5H-dibenzo[a,d]cyclohepten-5-yl)-4-thiouridine-5'-phosphate with dichloromethylenebisphosphonic acid (i) 5-(5-Hydroxy-(dibenzo(a,d)cyclohepten)-5-yl)-2',3',5'-tris-O-((1,1-dimethylethyl)dimethylsilyl)uridine was prepared from 2',3',5'-tris-O-((1,1-dimethylethyl)dimethylsilyl) uridine according to the method of Example 1 step (i) (using dibenzosuberenone instead of benzophenone) as a white foam.

MS: FAB(−ve): 791(M−1).

(ii) 5-(5H-Dibenzo[a,d]cyclohepten-5-yl)-2',3',5'-tris-O-((1,1-dimethylethyl)dimethylsilyl)uridine was prepared from the product of step (i) according to the method of Example 2 step (ii) as a colourless foam.

MS: FAB(−ve): 775(M−1).

(iii) 5-(5H-Dibenzo[a,d,]cyclohepten-5-yl)-2',3',5'-tris-O-((1,1-dimethylethyl)dimethylsilyl)-4-thiouridine was prepared from the product of step (ii) according to the method of Example 2 step (iii) as a yellow foam.

MS: FAB(−ve): 791(M−1).

(iv) The product of step (iii) (0.75 g) was dissolved in acetonitrile (10 ml) and treated with a 1:1 hydrofluoric acid-pyridine complex (6 ml). After 3 hours, the mixture was quenched with saturated aqueous sodium carbonate solution (100 ml) and the product was extracted into ethyl acetate. The organic phase was collected, dried over magnesium sulphate and the solvent was removed under reduced pressure. The residue was purified by flash silica-gel chromatography to afford 5-(5H-dibenzo[a,d]cyclohepten-5-yl)-4-thiouridine as a yellow powder (0.36 g).

MS: FAB(+ve): 451(M+1).

(v) The tetrasodium salt of the monoanhydride of 5-(5H-dibenzo[a,d]cyclohepten-5-yl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.13(d), 3.88(dd), −10.05(d);

MS: FAB (+ve): m/e 845/847/849 (M+1).

Example 5

5-(5H-Dibenzo[a,d]cyclohepten-5-yl)-4-thiouridine

Prepared as described in Example 4 step (iv).

$^1$H NMR δ (d$_6$-DMSO): 12.63(bs, 1H), 7.63(d, 1H), 7.58(d, 1H), 7.42–7.27(m, 6H), 7.02(m, 3H), 5.87(s, 1H), 5.71(d, 1H), 5.43(d, 1H), 5.18(d, 1H), 4.82(t, 1H), 3.76(m, 3H), 3.36(m, 1H), 3.27(m, 1H).

MS: FAB(+ve): 451(M+1).

Example 6

Tetrasodium salt of the monoanhydride of 5-(10,11-dihydro-5H-dibenzo[a,d]cyclohepten-5-yl)-4-thiouridine-5'-phosphate with dichloromethylenebisphosphonic acid (i) 5-((10,11-Dihydro-5-hydroxy-5H-dibenzo[a,d]cyclohepten)-5-yl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using dibenzosuberone instead of benzophenone) as a pale yellow oil.

MS: FAB(−ve): 793(M−1).

(ii) 5-(10,11-Dihydro-5H-dibenzo[a,d]cyclohepten-5-yl)-2',3',5'-tris-O-((1,1-dimethylethyl)dimethylsilyl)uridine was prepared from the product of step (i) according to the method of Example 2 step (ii) as a pale yellow foam.

MS: FAB(−ve): 777(M−1).

(iii) 5-(10,11-Dihydro-5H-dibenzo[a,d]cyclohepten-5-yl)-2',3',5'-tris-O-((1,1-dimethylethyl)dimethylsilyl)-4-thiouridine was prepared from the product of step (ii) according to the method of Example 2 step (iii) as a yellow foam.

MS: FAB(−ve): 793(M−1).

(iv) 5-(10,11-Dihydro-5H-dibenzo[a,d]cyclohepten-5-yl)-4-thiouridine was prepared from the product of step (iii) according to the method of Example 4 step (iv) as a yellow solid.

MS: APCI+loop: 453(M+1).

(v) The tetrasodium salt of the monoanhydride of 5-(10,11-dihydro-5H-dibenzo[a,d]cyclohepten-5-yl)-4-thiouridine-5'-phosphate with dichloromethylenebisphosphonic acid was prepared from the product of step (iv) according to the method of Example 1 step (iv) as a yellow solid.

$^{31}$P NMR δ (D$_2$O): 9.93(d), 3.67(dd), −9.38(d).

MS: FAB (+ve): 847/849/851 (M+1).

Example 7

5-(10,11-dihydro-5H-dibenzo[a,d]cyclohepten-5-yl)-4-thiouridine

Prepared as described in Example 6 step (iv).

$^1$H NMR δ (d$_6$-DMSO): 12.72(bs, 1H), 7.41(d, 1H), 7.35(d, 1H), 7.13(m, 7H), 5.78(d,1H), 5.6(s, 1H), 5.45(d, 1H), 5.15(d, 1H), 4.68(t, 1H), 3.79(q, 1H), 3.69(q, 1H), 3.64(m, 1H), 3.41(m, 2H), 3.18(m, 2H), 2.78(m, 2H), 2.78 (m, 2H).

MS: APCI+loop: 453(M+1).

Example 8

Tetrasodium salt of the monoanhydride of 5-(1,1-bis(4-methylphenyl)methyl)-4-thiouridine-5'-phosphate with dichloromethylenebisphosphonic acid (i) 5-(Hydroxy-1,1-bis(4-methylphenylmethyl)-2',3',5'-tris-O-((1,1-dimethylethyl)dimethylsilyl)uridine was prepared from 2',3',5'-tris-O-((1,1-dimethylethyl)dimethylsilyl) uridine according to the method of Example 1 step (i) (using 4,4'-dimethylbenzophenone instead of benzophenone) as a colourless foam.

MS: FAB(−ve): 795(M−1).

(ii) The product of step (i) (10.84 g) was dissolved in dichloromethane (100 ml), triethylsilane (2.6 ml) and treated with trifluoroacetic acid (2.1 ml). After stirring for 1 hour, the solvent was removed under reduced pressure and any remaining traces removed by azeotroping with toluene (two times). The residue was dissolved in dry dimethylformamide (80 ml) and treated with imidazole (1.77 g) and t-butyldimethylsilylchloride (2.11 g). After stirring for 16 hours, the mixture was quenched with water and the product extracted into ethyl acetate. The organic phase was collected and the solvent removed under reduced pressure. The residue was purified by flash silica-gel chromatography to afford 5-(1,1-bis(4-methylphenyl)methyl)-2',3',5'-tris-O-((1,1-dimethylethyldimethylsilyl)uridine as a colourless foam (8.59 g).

MS: FAB(−ve): 779(M−1).

(iii) 5-(1,1-Bis(4-methylphenyl)methyl)-2',3',5'-tris-O-((1,1-dimethylethyl)dimethylsilyl)-4-thiouridine was prepared from the product of step (ii) according to the method of Example 2 step (iii) as a yellow foam.

MS: FAB(−ve): 795(M−1).

(iv) 5-(1,1-Bis(4-methylphenyl)methyl)-4-thiouridine was prepared from the product of step (iii) according to the method of Example 4 step (iv) as a yellow solid.

MS: FAB(+ve): 455(M+1).

(v) The tetrasodium salt of the anhydride of 5-(1,1-bis(4-methylphenyl)methyl)-4-thiouridine-5'-phosphate with dichloromethylenebisphosphonic acid was prepared from the product of step (iv) according to the method of Example 1 step (iv) as a yellow powder.

$^{31}$P NMR δ (D$_2$O): 9.92(d), 3.71(dd), −9.35(d).

MS: FAB (+ve): 849/851/853 (M+1).

Example 9

Tetrasodium salt of the monoanhydride of 5-(1,1-bis(4-chlorophenyl)methyl)-4-thiouridine-5'-phosphate with dichloromethylenebisphosphonic acid (i) 5-(1,1-Bis(4-chlorophenyl)hydroxymethyl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using 4,4'-dichlorobenzophenone instead of benzophenone) to afford the product as a colourless foam.

MS: FAB(−ve): 836/838/840(M−1).

(ii) 5-(1,1-Bis(4-chlorophenyl)methyl)-2',3',5'-tris-O-((1,1-dimethylethyl)dimethylsilyl)uridine was prepared from the product of step (i) according to the method of Example 8 step (ii) as a colourless foam.

MS: FAB(−ve): 820/822/824(M−1).

(iii) 5-(1,1-Bis(4-chlorophenyl)methyl)-2',3',5'-tris-O-((1,1-dimethylethyl)dimethylsilyl)-4-thiouridine was prepared from the product of step (ii) according to the method of Example 2 step (iii) as a yellow foam.

MS: FAB(−ve): 836/838/840(M−1).

(iv) 5-(1,1-Bis(4-chlorophenyl)methyl)-4-thiouridine was prepared from the product of step (iii) according to the method of Example 4 step (iv) as a yellow solid.

MS: FAB(+ve): 495/497/499(M+1).

(v) The tetrasodium salt of the monoanhydride of 5-(1,1-bis(4-chlorophenyl)methyl)-4-thiouridine-5'-phosphate with dichloromethylenebisphosphonic acid was prepared from the product of step (iv) according to the method of Example 1 step (iv) as a yellow powder.

$^{31}$P NMR δ (D$_2$O): 9.40(d), 1.87(dd), −9.38(d);

MS: ESI-loop m/e: 399/400/401/402(M−2).

Example 10

The tetrasodium salt of the monoanhydride of 5-(1,1-bis(3,4-dichlorophenyl)methyl)-4-thiouridine-5'-phosphate with dichloromethylenebisphosphonic acid (i) To a solution of 3,4-dichloroiodobenzene (20 g) in dry tetrahydrofuran (300 ml) under a nitrogen atmosphere at −78° C. was added 1.7M t-butyllithium in pentane (86 ml), dropwise over 10 minutes. After 30 minutes, the yellow solution was briefly allowed to reach −30° C. by removing the cooling bath. The mixture was returned to −78° C. before adding quickly a solution of 3,4-dichlorobenzonitrile (13 g) in dry tetrahydrofuran (50 ml). The cooling bath was removed and the mixture allowed to reach room temperature. After 1 hour, the mixture was quenched with saturated aqueous ammonium chloride solution (300 ml). The mixture was stirred at room temperature for a further 16 hours and the product extracted into ethyl acetate. The solvent was removed under reduced pressure. The residue was purified by silica-gel chromatography eluting with diethyl ether:iso-hexane mixtures to afford 3,4,3',4'-tetrachlorobenzophenone as a beige solid. This was triturated with iso-hexane and filtered to afford a pure sample.

MS: EI: 318/320/322/324/326 (M$^+$).

(ii) 5-(1,1-Bis(3,4-dichlorophenyl)hydroxymethyl)-2',3',5'-tris-O-((1,1-dimethylethyl)dimethylsilyl)uridine was prepared from 2',3',5'-tris((1,1-dimethylethyl)dimethylsilyl)uridine according to the method of Example 1 step (i) (using the product of step (i) instead of benzophenone) as a pale yellow foam.

MS: APCI+loop: 887/889/891(M+H—H$_2$O).

(iii) 5-(1,1-Bis(3,4-dichlorophenyl)methyl)-2',3',5'-tris-O-((1,1-dimethylethyl)dimethylsilyl)uridine was prepared from the product of step (ii) according to the method of Example 2 step (ii) as a colourless foam.

MS: APCI+loop: 889/891/893(M+1).

(iv) 5-(1,1-Bis(3,4-dichlorophenyl)methyl)-2',3',5'-tris-O-((1,1-dimethylethyl)dimethylsilyl)-4-thiouridine was prepared from the product of step (iii) according to the method of Example 2 step (iii) as a yellow foam.

MS: FAB(−ve): 903/905/907/909(M−1).

(v) 5-(1,1-Bis(3,4-dichlorophenyl)methyl)-4-thiouridine was prepared from the product of step (ii) according to the method of Example 4 step (iv) as a yellow solid.

MS: FAB(−ve): 563/564/565/566(M−1).

(vi) The tetrasodium salt of the monoanhydride of 5-(1,1-bis(3,4-dichlorophenyl)methyl)-4-thiouridine-5'-phosphate with dichloromethylenebisphosphonic acid was prepared from the product of step (v) according to the method of Example 1 step (iii) as a yellow powder.

$^{31}$P NMR δ (D$_2$O): 9.56(d), 2.65(dd), −9.18(d).

MS: ESI-loop: 867/869/871/873/875(M−1).

Example 11

Tetrasodium salt of the monoanhydride of 5-(1,1-bis(4-methoxyphenyl)methyl)-4-thiouridine-5'-phosphate with dichloromethylenebisphosphonic acid (i) 5-(Hydroxy-1,1-bis(4-methoxyphenylmethyl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using 4,4'-dimethoxybenzophenone instead of benzophenone) as a colourless foam.

MS: FAB: 811(M+H—H$_2$O).

(ii) 5-(1,1-Bis(4-methoxyphenyl)methyl)-2',3',5'-tris-O-((1,1-dimethylethyl)dimethylsilyl)uridine was prepared from the product of step (i) according to the method of Example 2 step (ii) as colourless foam.

MS: FAB(+ve): 813(M+1), FAB(−ve): 811(M−1).

(iii) 5-(1,1-Bis(4-methoxyphenyl)methyl)-2',3',5'-tris-O-((1,1-dimethylethyl)dimethylsilyl)-4-thiouridine was prepared from the product of step (ii) according to the method of Example 2 step (iii) as a yellow foam.

MS: FAB(−ve): 827(M−1).

(iv) 5-(1,1-Bis(4-methoxyphenyl)methyl)-4-thiouridine was prepared from the product of step (iii) according to the method of Example 2 step (iv) as a yellow solid.

MS: APCI(+ve): 487(M+1).

(v) The tetrasodium salt of the monoanhydride of 5-(1,1-bis(4-methoxyphenyl)methyl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 8.98(d), 1.26(dd), −9.5(d).

MS: FAB(+ve): 859/861/863(M+1).

Example 12

Tetrasodium salt of the monoanhydride of 5-(3,6-dimethoxy-9H-fluoren-9-yl)-4-thiouridine-5'-phosphate with dichloromethylenebisphosphonic acid (i) 5-(3,6-Dimethoxy-9-hydroxyfluoren-9-yl)-2',3',5'-tris-O-((1,1-dimethylethyl)dimethylsilyl)uridine was prepared from 2',3',5'-tris-O-((1,1-dimethylethyl)dimethylsilyl) uridine according to the method of Example 1 step (i) (using 3,6-dimethoxyfluoren-9-one (J. Org. Chem. (1993) 58 (16), 4398–4404) instead of benzophenone) as a pale yellow solid.

$^1$H NMR: δ (CDCl$_3$): 8.40(s,1H), 7.32(d,2H), 7.06(d,2H), 6.72(dd, 2H), 5.75(d, 1H), 4.05(m,1H), 3.9(m, 1H), 3.83(m, 1H), 3.80(s, 6H), 3.45(m, 2H), 0.6(m, 27H), 0.0(m, 18H).

(ii) 5-(3,6-Dimethoxy-9H-fluoren-9-yl)-2',3',5'-tris-O-((1,1-dimethylethyl)dimethylsilyl)uridine was prepared from the product of step (i) according to the method of Example 2 step (ii) as a pale yellow powder.

MS: FAB(−ve): 696(M−1).

(iii) 5-(3,6-Dimethoxy-9H-fluoren-9-yl)-2',3',5'-tris-O-((1,1-dimethylethyl)dimethylsilyl)-4-thiouridine was prepared from the product of step (ii) according to the method of Example 2 step (iii) as a yellow foam and was used directly in the next step.

(iv) 5-(3,6-Dimethoxy-9H-fluoren-9-yl)-4-thiouridine was prepared from the product of step (iii) according to the method of Example 2 step (iv) as a yellow solid.

MS: FAB(+ve): 485(M+1).

(v) The tetrasodium salt of the monoanhydride of 5-(3,6-dimethoxy-9H-fluoren-9-yl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.71(d), 3.58(dd), −9.5(d).

MS: ESI–loop: 793/791/789(M−1).

Example 13

Tetrasodium salt of the monoanhydride of 5-(3-(4-methylphenoxy)phenylmethyl)-4-thiouridine-5'-phosphate with dichloromethylenebisphosphonic acid (i) 5-(Hydroxy-(3-((4-methylphenoxy)phenyl)methyl)-2',3',5'-tris-O-((1,1-dimethylethyl)dimethylsilyl)uridine was prepared from 2',3',5'-tris-O-((1,1-dimethylethyl) dimethylsilyl)uridine according to the method of Example 1 step (i) (using 3-(4-methylphenoxy)-benzaldehyde instead of benzophenone) as a colourless foam.

MS: FAB(−ve): 797(M−1).

(ii) 5-(3-(4-Methylphenoxy)phenylmethyl)-2',3',5'-tris-O-((1,1-dimethylethyl)dimethylsilyl)uridine was prepared from the product of step (i) according to the method of Example 2 step (ii) as a colourless oil.

MS: FAB(−ve): 781(M−1).

(iii) 5-(3-(4-Methylphenoxy)phenylmethyl)-2',3',5'-tris-O-((1,1-dimethylethyl)dimethylsilyl)-4-thiouridine was prepared from the product of step (ii) according to the method of Example 2 step (iii) as a yellow foam.

MS: APCI+loop: 799(M+1).

(iv) 5-(3-(4-Methylphenoxy)phenylmethyl)-4-thiouridine was prepared from the product of step (iii) according to the method of Example 2 step (iv) as a yellow foam.

MS: FAB: (+ve): 457(M+1).

(v) The tetrasodium salt of the monoanhydride of 5-(3-(4-methylphenoxy)phenylmethyl)-4-thiouridine-5'-phosphate with dichloromethylenebisphosphonic acid was prepared from the product of step (iii) according to the method of Example 1 step (iii) as a yellow powder.

$^{31}$P NMR δ (D$_2$O): 9.44(d), 3.45(dd), −9.78(d).

MS: FAB(+ve): 835/837/839(M+1).

Example 14

Tetrasodium salt of the monohydride of 5-(3-(4-chlorophenoxy)phenylmethyl)-4-thiouridine-5'-phosphate with dichloromethylenebisphosphonic acid (i) 5-((3-(4-Chlorophenoxy)phenyl)hydroxymethyl)-2',3',5'-tris-O-((1,1-dimethylethyl)dimethylsilyl)uridine was prepared from 2',3',5'-tris-O-((1,1-dimethylethyl)dimethylsilyl) uridine according to the method of Example 1 step (i) (using 3-(4-chlorophenoxy)-benzaldehyde instead of benzophenone) as a pale yellow oil.

$^1$H NMR δ (CDCl$_3$): 8.39(s,1H), 7.42(s,1H), 7.19–7.26 (m,5H), 7.00(m,1H), 6.79–6.85(m, 4H), 5.89–5.91(d, 1H), 5.48–5.49(d, 1H), 3.93–3.95(m, 2H), 3.55–3.67(m, 2H), 3.36–3.43(dd, 1H), 0.77–0.87(m, 27H), −0.14–0.07(m, 18H).

(ii) 5-(3-(4-Chlorophenoxy)phenylmethyl)-2',3',5'-tris-O-((1,1-dimethylethyl)dimethylsilyl)uridine was prepared from the product of step (i) according to the method of Example 2 step (ii) as a pale yellow foam and used directly in the next step.

(iii) 5-(3-(4-Chlorophenoxy)phenylmethyl)-2',3',5'-tris-O-((1,1-dimethylethyl)dimethylsilyl)-4-thiouridine was prepared from the product of step (ii) according to the method of Example 2 step (iii) as a yellow foam.

$^1$H NMR δ (CDCl$_3$): 9.32(s,1H), 7.38(s,1H), 7.22–7.15 (m,3H), 6.91–6.74(m,5H), 5.88–5.86(d,1H), 4.08–4.02(m, 1H), 3.97–3.93(m, 2H), 3.87–3.83(d, 1H), 3.80–3.76(d, 1H), 3.72–3.68(dd, 1H), 3.61–3.57(dd, 1H), 0.90–0.74(m, 27H), −0.12–0.6(m,18H).

(iv) 5-(3-(4-Chlorophenoxy)phenylmethyl)-4-thiouridine was prepared from the product of step (iii) according to the method of Example 2 step (iv) as a yellow solid.

MS: APCI–loop: 475/477(M−1).

(v) The tetrasodium salt of the monoanhydride of 5-(3-(4-chlorophenoxy)phenylmethyl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.9(d), 3.7(dd), −9.45(d).

MS: ESI–loop: 390/391/392(M$^{2-}$).

Example 15

Tetrasodium salt of the monoanhydride of 5-(3-(3,4-dichlorophenoxy)phenylmethyl)-4-thiouridine-5'-phosphate with dichloromethylenebisphosphonic acid (i) 5-((3-(3,4-Dichlorophenoxy)phenyl)hydroxymethyl)-2',3',5'-tris-O-((1,1-dimethylethyl)dimethylsilyl)uridine was prepared from 2',3',5'-tris-O-((1,1-dimethylethyl) dimethylsilyl)uridine according to the method of Example 1 step (i) (using 3-(3,4-dichlorophenoxy)benzaldehyde instead of benzophenone) as a colourless foam.

$^1$H NMR δ (CDCl$_3$): 8.3 (m, 0.5H), 7.6 (2xs, 0.5H), 7.4–6.8 (m, 7H), 6.0 (t, 0.5H), 5.6 (m, 0.5H), 4.7 (s, 0.5H), 4.1 (m, 2H), 4.0 (d, 1H), 3.7 (m, 1H), 3.5 (m, 0.5H), 0.9 (m, 27H), 0.0 (m, 18H) mixture of diastereoisomers 60/40

(ii) 5-(3-(3,4-Dichlorophenoxy)phenylmethyl)-2',3',5'-tris-O-((1,1-dimethylethyl)dimethylsilyl)uridine was prepared from the product of step (i) according to the method of Example 2 step (ii) as a colourless foam and was used directly in the next step.

(iii) 5-(3-(3,4-Dichlorophenoxy)phenylmethyl)-2',3',5'-tris-O-((1,1-dimethylethyl)dimethylsilyl)-4-thiouridine was prepared from the product of step (ii) according to the method of Example 2 step (iii) as a yellow foam.

$^1$H NMR δ (CDCl$_3$): 9.3(s,1H), 7.43(bs,1H), 7.25–7.3(m, 1H), 7.15–7.25(m, 1H), 7.0–6.9(m, 2H), 6.9–6.7 (m, 3H), 5.9(bs, 1H), 4.15–3.5(m, 7H), 0.83(s, 9H), 0.78(s, 9H), −0.2–0.5(m, 18H).

(iv) 5-(3-(3,4-Dichlorophenoxy)phenylmethyl)-4-thiouridine was prepared from the product of step (iii) according to the method of Example 2 step (iv) as a yellow solid.

$^1$H NMR δ (d$_6$-DMSO): 12.75(bs,1H), 8.07(bs,1H), 7.61 (d, 1H), 7.31(t, 1H), 7.25(d, 1H), 7.09(d, 1H), 7.02(bs, 1H), 6.96(dd, 1H), 6.88(dd, 1H), 5.73(d, 1H), 5.49(d, 1H), 5.15(t, 1H), 5.10(d, 1H), 4.04(q, 1H), 3.96(q, 1H), 3.90–3.85(m, 1H), 3.8(bs, 2H), 3.7–3.6(m, 1H), 3.55–3.45(m, 1H).

(v) The tetrasodium salt of the monoanhydride of 5-(3-(3,4-dichlorophenoxy)phenylmethyl)-4-thiouridine-5'-phosphate with dichloromethylenebisphosponic acid was prepared from the product of step (iv) according to the method of Example 1 step (iii) as a yellow powder.

$^{31}$P NMR δ (D$_2$O): 10.12(d), 3.97(dd), −9.2(d).

MS: ESI–loop: 815/819/821.

Example 16

Tetrasodium salt of the monoanhydride of 5-(3-(4-methoxyphenoxy)phenylmethyl)-4-thiouridine-5'-phosphate with dichloromethylenebisphosphonic acid (i) 5-(Hydroxy-(3-((4-methoxyphenoxy)phenyl)methyl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using 3-(4-methoxyphenoxy)benzaldehyde instead of benzophenone) as a colourless foam.

$^1$H NMR δ (CDCl$_3$): 8.26(bs, 1H), 7.38(d, 1H), 6.7–7.1 (m, 7H), 5.9–5.86(m, 1H), 5.49–5.46(m, 1H), 4.57(bs, 1H), 4.05–4.00(m, 1H), 4.95–4.90(m, 2H), 3.73(s, 3H), 3.7–3.5 (m, 2H), 3.9–3.8(m, 1H), 0.86(s, 9H), 0.83(s, 9H), 0.73(s, 9H), −0.2–0.05(s, 18H).

(ii) 5-(3-(4-Methoxyphenoxy)phenylmethyl)-2',3',5'-tris-O-((1,1-dimethylethyl)dimethylsilyl)uridine was prepared from the product of step (i) according to the method of Example 2 step (ii) as a colourless foam.

$^1$H NMR δ (CDCl$_3$): 8.21 (bs, 1H), 7.31(s, 1H), 7.09(t, 1H), 6.7–6.9(m, 6H), 6.66(dd, 1H), 5.89(d, 1H), 4.05(m, 1H), 3.9(m, 2H), 3.7(s, 3H), 3.68(dd, 1H), 3.58(dd, 1H), 3.55(m, 2H), 0.82(m, 18H), 0.78(s, 9H), −0.2–0.05(m, 18H).

(iii) 5-(3-(4-Methoxyphenoxy)phenylmethyl)-2'3',5'-tris-O-((1,1-dimethylethyl-dimethylsilyl)-4-thiouridine was prepared from the product of step (ii) according to the method of Example 2 step (iii) as a yellow foam.

$^1$H NMR δ (CDCl$_3$): 9.29(bs, 1H), 7.3(s, 1H), 7.11(t, 1H), 6.75–6.9(m, 6H), 6.69(dd, 1H), 5.85(d, 1H), 4.03(m, 1H), 3.98(m, 2H), 3.83(d, 1H), 3.76(d, 1H), 3.72(s, 3H), 3.66(dd, 1H), 3.56(dd, 1H), 0.84(s, 9H), 0.82(s, 9H), 0.79(s, 9H), −0.2–0.05(m, 18H).

(iv) 5-(3-(4-Methoxyphenoxy)phenylmethyl)-4-thiouridine was prepared from the product of step (iii) according to the method of Example 2 step (iv) as a yellow solid.

$^1$H NMR δ (CDCl$_3$): 11.13(bs, 1H), 7.26(s, 1H), 7.15(t, 1H), 6.75–7.0(m, 6H), 6.78(dd, 1H), 5.70(d, 1H), 4.78(bs, 1H), 4.30–4.25(m, 1H), 4.25–4.15(m, 2H), 4.07(m, 1H), 3.8–3.5(m, 4H), 3.75(s, 3H).

(v) The tetrasodium salt of the monoanhydride of 5-(3-(4-methoxyphenoxy)phenylmethyl)-4-thiouridine-5'-phosphate with dichloromethylenebisphosphonic acid was prepared from the product of step (iv) according to the method of Example 1 step (iii).

$^{31}$P NMR δ (D$_2$O): 10.05(d), 3.95(dd), −9.27(d).

MS: ESI–loop: 777/779/781

Example 17

Tetrasodium salt of the monoanhydride of 5-((3-methoxy-4-phenylmethoxy)phenylmethyl)-4-thiouridine-5'-phosphate with dichloromethylenebisphosphonic acid (i) 5-(Hydroxy-((3-methoxy-4-phenylmethoxy)phenyl)methyl)-2',3',5'-tris-O-((1,1-dimethylethyl)dimethylsilyl) uridine was prepared from 2',3',5'-tris-O-((1,1-dimethylethyl-dimethylsilyl)uridine according to the method of Example 1 step (i) (using 3-methoxy-4-phenylmethoxybenzaldehyde instead of benzophenone) as a colourless foam.

$^1$H NMR δ (CDCl$_3$): 8.3(bs, 1H), 7.2–7.45(m, 6H), 6.94 (bs, 1H), 6.85–6.75(m, 2H), 5.45(d, 1H), 5.07(s, 2H), 4.03 (m, 1H), 3.6–3.55(m, 1H), 3.24(d, 1H), 0.82(s, 9H), 0.81(s, 9H), 0.76(s, 9H), −0.15–0.01 (m, 18H).

(ii) 5-((3-Methoxy-4-phenylmethoxy)phenylmethyl)-2', 3',5'-tris-O-((1,1-dimethylethyl)dimethylsilyl)uridine was prepared from the product of step (i) according to the method of Example 2 step (ii) as a colourless foam.

$^1$H NMR δ (CDCl$_3$): 8.27(bs, 1H), 7.2–7.4(m, 6H), 6.71 (d, 1H), 6.67(d, 1H), 6.54(dd, 1H), 5.86(d, 1H), 5.02(s, 2H), 4.03(m, 2H), 3.98(m, 2H), 3.76(s, 3H), 3.71(dd, 1H), 3.64 (dd, 1H), 3.46(d, 1H), 3.51(d, 1H), 0.82(s, 9H), 0.81(s, 9H) 0.75(s, 9H), −0.2–0.0(m, 18h).

(iii) 5-((3-Methoxy-4-phenylmethoxy)phenylmethyl)-2', 3',5'-tris-O-((1,1-dimethylethyl)dimethylsilyl)-4-thiouridine was prepared from the product of step (ii) according to the method of Example 2 step (iii) as a yellow foam.

$^1$H NMR δ (CDCl$_3$): 9.31 (bs, 1H), 7.36(d, 2H), 7.25–7.35(m, 3H), 7.23(d, 1H), 6.76(d, 1H), 6.70(d, 1H), 6.54(dd, 1H), 5.83(d, 1H), 5.05(s, 1H), 4.07(m 1H), 3.97(m, 2H), 3.79(s, 3H), 3.78(m, 1H), 3.71(dd, 1H), 3.6(dd, 1H), 0.84(s, 9H), 0.83(s, 9H), 0.79(s, 9H), −0.2–0.05(m, 18H).

(iv) 5-((3-Methoxy-4-phenylmethoxy)phenylmethyl)-4-thiouridine was prepared from the product of step (iii) according to the method of Example 2 step (iv) as a yellow solid.

$^1$H NMR δ (CDCl$_3$): 11.09(bs, 1H), 7.25–7.5(m, 5H), 7.14(s, 1H), 6.72–6.68(m, 2H) 6.65(d, 1H), 5.66(d, 1H), 5.07(s, 2H), 4.67(bs, 1H), 4.23(m, 1H), 4.07(m, 2H), 3.99(s, 1H), 3.81(s, 3H), 3.75–3.65(m, 2H), 3.6–3.4(m, 2H).

(v) The tetrasodium salt of the monoanhydride of 5-((3-methoxy-4-phenylmethoxy)phenylmethyl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.25(d), 1.75(dd), −9.66(d).

MS: FAB: 881 (M+1).

Example 18

Tetrasodium salt of the monoanhydride of 5-((4-methoxy-3-phenylmethoxy)phenylmethyl)-4-thiouridine-5'-phosphate with dichloromethylenebisphosphonic acid (i) 5-(Hydroxy((4-methoxy-3-phenylmethoxy)phenyl) methyl)-2',3',5'-tris-O-((1,1-dimethylethyl)dimethylsilyl)

uridine was prepared from 2',3',5'-tris-O-((1,1-dimethylethyl-dimethylsilyl)uridine according to the method of Example 1 step (i) (using 4-methoxy-3-phenylmethoxybenzaldehyde instead of benzophenone) as a colourless foam.

MS: FAB(−ve): 827(M−1).

(ii) 5((4-Methoxy-3-phenylmethoxy)phenylmethyl)-2',3',5'-tris-O-((1,1-dimethylethyl)dimethylsilyl)uridine was prepared from the product of step (i) according to the method of Example 2 step (ii) as colourless foam.

$^1$H NMR δ (CDCl$_3$): 8.49(s, 1H), 7.36–7.16(m, 6H), 6.73–6.62(m, 3H), 5.86(d, 1H), 5.00(s, 2H), 4.04(m, 1H), 3.93(m, 2H), 3.74(s, 3H), 3.74–3.58(s, 2H), 3.45(s, 2H), 0.86–0.75(m, 27H), 0.0–0.16(m, 18H).

(iii) 5((4-Methoxy-3-phenylmethoxy)phenylmethyl)-2',3',5'-tris-O-((1,1-dimethylethyl)dimethylsilyl)-4-thiouridine was prepared from the product of step (ii) according to the method of Example 2 step (iii) as a yellow foam.

MS: FAB(−ve): 827(M−1).

(iv) 5-((4-Methoxy-3-phenylmethyloxy)phenylmethyl)-4-thiouridine was prepared from the product of step (iii) according to the method of Example 4 step (iv) as a yellow solid.

MS: FAB(+ve): 487(M+1).

(v) The tetrasodium salt of the monoanhydride of 5-((4-methoxy-3-phenylmethoxy)phenylmethyl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.55(d), 2.66(dd), −9.60(d).

MS: ESI–loop: 791/793/795(M−1).

Example 19

Tetrasodium salt of the monoanhydride of 5-(4-butoxyphenylmethyl)-4-thiouridine-5'-phosphate with dichloromethylenebisphosphonic acid (i) 5-((4-Butoxyphenyl)hydroxymethyl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using 4-butoxybenzaldehyde instead of benzophenone) as a colourless foam.

$^1$H NMR δ (CDCl$_3$): 8.26(s, 1H), 7.36(s, 1H), 7.2(d, 1H), 6.80(d, 1H), 5.88(d, 1H), 5.49(d, 1H), 4.00(m, 1H), 3.93(m, 2H), 3.66(dd, 1H), 3.55dd, 1H), 3.26(d, 1H), 1.67(m, 2H), 1.40(m, 2H), 0.80(m, 30H), 0.00(m, 18H).

(ii) 5-(4-Butoxyphenylmethyl)-2',3',5'-tris-O-((1,1-dimethylethyl)dimethylsilyl)uridine was prepared from the product of step (i) according to the method of Example 2 step (ii) as a pale yellow foam.

$^1$H NMR δ (CDCl$_3$): 7.94(s, 1H), 7.16(s, 1H), 7.0(d, 2H), 6.7(d, 2H), 5.83(d, 1H), 4.0(m, 1H), 3.93(m, 2H), 3.82(t, 2H), 3.6(dd, 1H), 3.47(d, 1H), 1.63(m, 2H), 1.34–1.41(m, 2H), 0.73–0.88(m, 30H), −0.15–0.00(m, 18H).

(iii) 5-(4-Butoxyphenylmethyl)-2',3',5'-tris-O-((1,1-dimethylethyl)dimethylsilyl)-4-thiouridine was prepared from the product of step (ii) according to the method of Example 2 step (iii) as a yellow foam.

$^1$H NMR δ (CDCl$_3$): 9.31(s, 1H), 7.19(s, 1H), 7.0(d, 2H), 6.73(d, 2H), 5.84(d, 1H), 4.02(m, 1H), 3.95(m, 1H), 3.90(m, 1H), 3.85(t, 2H), 3.76(d, 1H), 3.66(m, 1H), 3.56(m, 1H), 1.67(m, 2H), 1.38(m, 2H), 0.9(t, 3H), 0.83(m, 27H), −0.08–0.08 (m, 18H).

(iv) 5-(4-Butoxyphenylmethyl)-4-thiouridine was prepared from the product of step (iii) according to the method of Example 2 step (iv) as a yellow solid.

MS: FAB: (+ve): 423(M+1).

(v) The tetrasodium salt of the monoanhydride of 5-(4-butoxyphenylmethyl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.80(d), 3.66(dd), −9.5(d).

MS: ESI–loop: 363 (M)$^{2-}$.

Example 20

Tetrasodium salt of the monoanhydride of 5-(9-ethylcarbazol-3-ylmethyl)-4-thiouridine-5'-phosphate with dichloromethylenebisphosphonic acid (i) 5-((9-Ethylcarbazol-3-yl)hydroxymethyl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using 9-ethyl-3-carbazolecarboxaldehyde instead of benzophenone) as a yellow foam.

$^1$H NMR δ (CDCl$_3$): 8.4(d, 1H), 8.10(m, 2H), 7.4(m, 5H), 7.2(t, 2H), 5.95(t, 1H), 5.83(m, 1H), 4.35(q, 2H), 4.17(m, 1H), 4.00(m, 2H), 3.60(m, 2H), 3.28–3.43(dd, 1H), 1.43(m, 3H).

(ii) The product of step (i) (15.83 g) was subjected to hydrogenolysis at 2.5 atmospheres in ethanol (200 ml) using 10% palladium on charcoal (1 g) until reaction was complete by thin layer chromatographical analysis. The catalyst was filtered and the mother liquor collected. The solvent was removed under reduced pressure. The remaining residue was purified by flash silica-gel chromatography to afford 5-(9-ethylcarbazol-3-ylmethyl)-2',3',5'-tris-O-((1,1-dimethylethyl)dimethylsilyl)uridine as a yellow foam.

MS: FAB(−ve): 792(M−1).

(iii) 5-(9-Ethylcarbazol-3-ylmethyl)-2',3',5'-tris-O-((1,1-dimethylethyl)dimethylsilyl)-4-thiouridine was prepared from the product of step (ii) according to the method of Example 2 step (iii) as a yellow foam.

$^1$H NMR δ CDCl$_3$): 9.49(s, 1H), 8.05(d, 1H), 7.93(s, 1H), 7.49(t, 1H), 7.40(d, 1H), 7.34(m, 3H), 7.20(t, 1H), 5.91 (m, 1H), 4.35(q, 2H), 4.11(m, 2H), 4.09(m, 1H), 4.01(m, 1H), 3.96(m, 1H), 3.68(dd, 1H), 3.58(dd, 1H), 1.28(t, 3H), 0.83–0.96(m, 27H), 0.00–0.15(m, 18H).

(iv) 5-(9-Ethylcarbazol-3-ylmethyl)-4-thiouridine was prepared from the product of step (iii) according to the method of Example 2 step (iv) as a yellow solid.

MS: FAB(+ve): 468(M+1).

(v) The tetrasodium salt of the monoanhydride of 5-(9-ethylcarbazol-3-ylmethyl)-4-thiouridine-5'-phosphate with dichloromethylenebisphosphonic acid was prepared from the product of step (iv) according to the method of Example 1 step (iii) as a yellow powder.

$^{31}$P NMR δ (D$_2$O): 9.65(d), 3.0(dd), −9.45(d).

MS: FAB(+ve): 840/842/844(M+1).

Example 21

Tetrasodium salt of the monoanhydride of 5-((4-phenyl)phenylthio)-4-thiouridine-5'-phosphate with dichloromethylenebisphosphonic acid (i) 5-((4-Phenyl)phenylthio)-2',3',5'-tris-O-((1,1-dimethylethyl)dimethylsilyl)uridine was prepared from 2',3', 5'-tris-O-((1,1-dimethylethyl)dimethylsilyl)uridine according to the method of Example 1 step (i) (using (4-phenyl) phenyldisulphide (J. Chem. Soc. Perkin Trans. I 1983, (11), 2605–2609) instead of benzophenone) as a colourless foam.

MS: FAB(+ve): 771(M+1).

(ii) 5-((4-Phenyl)phenylthio)-2',3',5'-tris-O-((1,1-dimethylethyl)dimethylsilyl)-4-thiouridine was prepared from the product of step (i) according to the method of Example 2 step (iii) as a yellow foam.

MS: FAB(+ve): 787(M+1).

(iii) 5((4-Phenyl)phenylthio)-4-thiouridine was prepared from the product of step (ii) according to the method of Example 6 step (iv) as a yellow foam.

MS: FAB(+ve): 445(M+1).

(v) The tetrasodium salt of the monoanhydride of 5-((4-Phenyl)phenylthio)-4-thiouridine-5'-phosphate with dichloromethylenebisphosphonic acid was prepared from the product of step (iii) according to the method of Example 1 step (iii) as a yellow powder.

$^{31}$P NMR δ (D$_2$O): 9.60(d), 2.71(dd), −9.30(d).

MS: ESI–loop: 749/751/753.

Example 22

Tetrasodium salt of the monoanhydride of 5-(9-methoxyfluoren-9-yl)uridine-5'-phosphate with dichloromethylenebisphosphonic acid (i) The product of Example 2 step (i) (10 g) was dissolved in dry 1,2-dichloroethane (60 ml) and treated with methanol (5.2 ml) and 1M zinc dichloride solution in diethyl ether (100 ml) at room temperature. After 16 hours the mixture was concentrated to about 15 ml and 1,2-dichloroethane (40 ml) was added. After stirring for 3 hours ethyl acetate (300 ml) and water (50 ml) was added. The organic phase was collected and again washed with water (50 ml). The organic phase was dried over magnesium sulphate and the solvent removed under reduced pressure. The residue was purified by flash silica-gel chromatography to afford 5-(9-methoxyfluoren-9-yl)-2',3',-bis-O-((1,1-dimethylethyl) dimethylsilyl)uridine as a colourless foam (5.8 g).

$^1$H NMR δ (CDCl$_3$): 7.96(s, 1H), 7.63(bs, 1H), 7.54(d, 2H), 7.2–7.5(m, 2H), 7.10(m, 4H), 5.35(d, 1H), 4.66(dd, 1H), 4.09(dd, 1H), 3.97(bs, 1H), 3.74(d, 1H), 3.55(t, 1H), 3.37(dd, 1H), 2.64(s, 3H), 0.79(s, 9H), 0.82(s, 9H), −0.1–0.05(s, 12H).

(ii) 5-(9-Methoxyfluoren-9-yl)uridine was prepared from the product of step (i) according to the method of Example 2 step (iv) as a colourless foam.

$^1$H NMR δ (d$_6$-DMSO): 11.06(bs, 1H), 8.4(s, 1H), 7.9(d, 2H), 7.35–7.45(m, 2H), 7.2–7.3(m, 4H), 5.88(d, 1H), 5.46 (d, 1H), 5.16(d, 1H), 5.04(t, 1H), 4.17(q, 1H), 4.03(m, 1H), 3.93(m, 1H), 3.70(m, 1H), 3.60(m, 1H), 2.61(s, 3H).

(iii) The tetrasodium salt of the monoanhydride of 5-(9-methoxyfluoren-9-yl)uridine-5'phosphate with dichloromethylenebisphosphonic acid was prepared from the product of step (ii) according to the method of Example 1 step (iii) as a white powder.

$^{31}$P NMR δ (D$_2$O): 9.70(d), 3.60(dd), −9.40(d).

MS: FAB(+ve): 811/813/815(M+1).

Example 23

Tetrasodium salt of 5-((4-phenyl)phenylcarbonyl) uridine-5'-phosphate, monoanhydride with dichloromethylenebisphosphonic acid (i) 5-((4-Phenyl)phenylcarbonyl)-2',3',5'-tris-O-((1,1-dimethylethyl)dimethylsilyl)uridine was prepared from 2',3', 5'-tris-O-((1,1-dimethylethyl)dimethylsilyl)uridine according to the method of Example 1 step (i) (using (4-phenyl) phenylcarbonyl chloride instead of benzophenone) as a colourless foam.

$^1$H NMR δ (CDCl$_3$): 8.22(s, 1H), 8.21(s, 1H), 7.82(dd, 2H), 7.63(dd, 2H), 7.60(d, 2H), 7.40(m, 3H), 6.09(d, 1H), 4.18(m, 1H), 4.03(m, 2H), 3.83(dd, 1H), 3.69(dd, 1H), 0.93(s, 9H), 0.89(s, 9H), 0.8(s, 9H), −0.05–0.1 (m,18H).

(ii) 5-((4-Phenyl)phenylcarbonyl)uridine was prepared from the product of step (i) according to the method of Example 2 step (iv) as a colourless foam.

$^1$H NMR δ (d$_6$-DMSO): 11.67(s, 1H), 8.56(s, 1H), 7.85(d, 2H), 7.78(d, 2H), 7.75(d, 2H), 7.51(t, 2H),7.43(t, 1H), 5.82(d, 1H), 5.50(d, 1H), 5.11(d, 1H), 5.05(t, 1H), 4.12(q, 1H), 4.0(dd, 1H), 3.90(m, 1H), 3.63(m, 1H), 3.50(m, 1H).

(iii) The tetrasodium salt of the monoanhydride of 5-((4-phenyl)phenylcarbonyl)uridine-5'-phosphate with dichloromethylenebisphosphonic acid was prepared from the product of step (ii) according to the method of Example 1 step (iii) as a white powder.

$^{31}$P NMR δ (D$_2$O): 9.9(d), 3.8(dd), −9.15(d).

MS: ESI–loop: 729(M−H).

Example 24

Trisodium salt of 5-diphenylmethyluridine-5'-(tetrahydrogen-triphosphate)-P$^3$-monomethyl ester.

(i) 5-diphenylmethyluridine was prepared according to the method of Example 1 steps (i) and (ii) as a white solid (4 g).

MS: FAB: m/e 411 (M+1).

(ii) The product of step (i) (2.0 g) and 1,8-bis (dimethylamino)naphthalene (1.7 g) were dissolved in dry trimethylphosphate (20 ml) and cooled to 0° C. under a nitrogen atmosphere. Phosphorous oxychloride (0.55 ml) was added dropwise and the resulting mixture stirred at low temperature for 3 hours before addition of bis(tri-n-butylammonium)pyrophosphate (50 ml of a 0.5M solution in dimethylformamide) and tri-n-butylamine (5.1 ml). After 5 minutes the reaction was quenched by addition of aqueous triethylammonium bicarbonate solution (300 ml of a 0.2M solution) and stirred for 15 minutes before being extracted three times with ethyl acetate (100 ml). The aqueous phase was concentrated under reduced pressure and the residue purified by reverse phase chromatography (C-18 Sep-pak silica) eluting with water. Fractions containing product were pooled and lyophilised to leave 5 -diphenylmethyluridine-5'-triphosphate tetrakistriethylammonium salt as a colourless gum (2.0 g).

$^{31}$P NMR: δ (D$_2$O): −4.8(d), −9.7(d), −21.0(t).

(iii) The product of step (ii) (2.0 g) was dissolved in dry pyridine (30 ml) and concentrated to dryness under reduced pressure three times and then dissolved in dry pyridine (20 ml) and tri-n-octylamine (1.7 ml) and again was evaporated to dryness under reduced pressure. The resulting gum was slurried in dry 1,4-dioxane (30 ml) under a nitrogen atmosphere and treated with tri-n-butylamine (0.9 ml) and diphenylphosphochloridate (0.6 ml) with further stirring at room temperature for 2.5 hours. The solvents were evaporated under reduced pressure. Dry diethyl ether (50 ml) and iso-hexane (200 ml) were added and the mixture cooled to 0° C. under nitrogen atmosphere with stirring for 30 minutes. The supernatant was decanted and the remaining gum dissolved in 1,4-dioxane (10 ml) and evaporated to dryness under reduced pressure. The resulting gum was dissolved in dry pyridine (20 ml) under a nitrogen atmosphere and treated with dry methanol (10 ml) and the resulting solution allowed to stir at room temperature for 2.5 hours. The volatiles were removed by evaporation under reduced pressure and the remaining residue partitioned between water (50 ml) and diethyl ether (50 ml). The aqueous phase containing the product was purified by reverse phase chromatography (C-18 Sep-pak silica) eluting with water. Fractions containing product were pooled, lyophilised and the residue was dissolved in water and passed down an ion-exchange column (Dowex-50 $Na^+$ form) eluting with water. UV (254 nm) active fractions were pooled, lyophilised and the residue was purified by reverse phase chromatography (C18 Sep-pak silica) eluting with water. Fractions containing product were pooled and lyophilised to leave 5-diphenylmethyluridine-5'-(tetrahydrogen triphosphate)-$P^3$-monomethyl ester, trisodium salt as a white powder (0.07 g).

$^-$P NMR δ ($D_2O$): −7.95(d), −10.0(d), −21.4(t).

MS: (FAB) (+ve): m/e 731 (M+H)$^+$

Example 25

Trisodium salt of 5-diphenylmethyluridine-5'-(tetrahydrogen-triphosphate)-$P^3$-mono(n-propyl) ester (i) The product of Example 24, step (ii) (which was 5-diphenylmethyluridine-5'-triphosphate tetrakistriethylammonium salt) (2.35 g) was dissolved in dry pyridine (50 ml) and concentrated to dryness under reduced pressure three times and then dissolved in dry pyridine (50 ml) and tri-n-octylamine (1.95 ml) and again this was evaporated to dryness under reduced pressure. The resulting gum was slurried in dry 1,4-dioxane (40 ml) under a nitrogen atmosphere and treated with tri-n-butylamine (1.06 ml) and diphenylphosphochloridate (0.693 ml) with further stirring at room temperature for 2.5 hours. The solvents were evaporated under reduced pressure. Dry diethyl ether (50 ml) and iso-hexane (150 ml) were added and the mixture stirred under a nitrogen atmosphere for 5 minutes. The supernatant was decanted and the remaining gum dissolved in dry pyridine (40 ml).

(ii) 20 ml of this solution was removed by dry syringe and added to a round bottom flask under nitrogen containing dry n-propanol (10 ml). The mixture was stirred at room temperature for a further 16 hours before removing the solvent under reduced pressure and partitioning the residue between ether and water. The aqueous phase was separated and lyophilised. The resulting residue was purified by reverse phase chromatography (C-18 Sep-pak silica) eluting with water. Fractions containing product were pooled. lyophilised and the residue was dissolved in water and passed down an ion-exchange column (Dowex-50 $Na^+$ form) eluting with water. The UV (254 nm) active fractions were pooled, lyophilised and the residue was purified by reverse phase chromatography (C18 Sep-pak silica) eluting with water. The fractions which contained the product were pooled and lyophilised to leave the trisodium salt of 5-diphenylmethyluridine-5'-(tetrahydrogen-triphosphate)-$P^3$-mono(n-propyl)ester as a white solid (0.09 g).

$^{31}$P NMR δ ($D_2O$): −9.40(d), −10.34(d), −21.74(t).

MS: ESI (−ve): 691 (M−3$Na^+$ +2H).

Example 26

Trisodium salt of 5-diphenylmethyluridine-5'-(tetrahydrogen-triphosphate)-$P^3$-mono(2-methoxyethyl)ester.

20 ml of the solution which was the product of step (i) of Example 25 was removed by dry syringe and added under nitrogen to a round bottom flask containing dry 2-methoxy ethanol (10 ml). The mixture was stirred at room temperature for a further 16 hours before removing the solvent under reduced pressure and partitioning the residue between ether and water. The aqueous layer was separated and lyophilised. The resulting residue was purified by reverse phase chromatography (C-18 Sep-pak silica) eluting with water. Fractions containing the product were pooled, lyophilised and the residue was dissolved in water and passed down an ion-exchange column (Dowex-50 $Na^+$ form) eluting with water. The UV (254 nm) active fractions were pooled, lyophilised and the residue was purified by reverse phase chromatography (C18 Sep-pak silica) eluting with water. The fractions which contained the product were pooled and lyophilised to leave the trisodium salt of 5-diphenylmethyluridine-5'-(tetrahydrogen triphosphate)-$P^3$-mono(2-methoxyethyl)ester as a white powder (0.053 g).

$^{31}$P NMR δ ($D_2O$): −9.56(d), −10.23(d), −21.60(t).

MS: ESI (−ve): 707 (M−3$Na^+$ +2H).

Example 27

Trisodium salt of 5-diphenylmethyluridine-5'-(tetrahydrogen-triphosphate)-$P^3$-monophenylmethyl ester The product of Example 24, step (ii) (which was 5-diphenylmethyluridine-5'-triphosphate-tetrakistriethylammonium salt), (0.58 g) was dissolved in dry pyridine (30 ml) and concentrated to dryness under reduced pressure three times and then dissolved in dry pyridine (30 ml) and tri-n-octylamine (0.48 ml) and again was evaporated to dryness under reduced pressure. The resulting gum was slurried in dry 1,4-dioxane (15 ml) under a nitrogen atmosphere and treated with tri-n-butylamine (0.26 ml) and diphenylphosphochloridate (0.171 ml) with further stirring at room temperature for 2.5 hours. The solvents were evaporated under reduced pressure. Dry diethyl ether (50 ml) and iso-hexane (150 ml) were added and the mixture stirred under a nitrogen atmosphere for 2 minutes. The supernatant was decanted and the remaining gum dissolved in dry pyridine (15 ml) and treated with phenylmethyl alcohol (7 ml). The mixture was stirred at room temperature for a further 16 hours before removing the solvent under reduced pressure and partitioning the residue between ether and water. The aqueous phase was separated and lyophilised. The resulting residue was purified by reverse phase chromatography (C-18 Sep-pak silica) eluting with 0.1M aqueous triethylammonium bicarbonate solution. Fractions containing product were pooled, lyophilised and the residue was dissolved in water and passed down a ion-exchange column (Dowex-50 $Na^+$ form) eluting with water. The UV (254 nm) active fractions were pooled, lyophilised and the residue was purified by reverse phase chromatography (C18 Sep-pak silica) eluting with water. The fractions which contained the product were pooled and lyophilised to leave the trisodium salt of 5-diphenylmethyluridine 5'-(tetrahydrogen triphosphate)-$P^3$-monophenylmethyl ester as a white solid (0.031 g).

$^{31}$P NMR δ ($D_2O$): −9.62(d), −10.00(d), −21.44(t).

MS: ESI (loop): 739 (M−3$Na^+$ +2H).

Example 28

Trisodium salt of 5-diphenylmethyl-4-thiouridine-5'-(tetrahydrogen-triphosphate)-$P^3$-monomethyl ester (i) The product of Example 1 step (i), (5-(hydroxy-(1,1-diphenyl)methyl)-2',3',5'-tris-O-((1,1-dimethylethyl)

dimethylsilyl)uridine) (6.8 g), was dissolved in dichloromethane (80 ml) and triethylsilane (1.83 ml) and treated with trifluoroacetic acid (1.38 ml). After stirring for 20 minutes the solvents were removed under reduced pressure and any remaining traces removed by azeotroping three times with toluene. The remaining residue was dissolved in dimethylformamide (5 ml) and treated with imidazole (0.54 g) and t-butyldimethylsilylchloride (0.6 g). After stirring for 16 hours the mixture was partitioned between water and iso-hexane and the organic phase was washed with water, collected and dried over magnesium sulphate. The solvent was removed under reduced pressure and the residue was purified by flash silica-gel chromatography eluting with ethyl acetate/iso-hexane mixtures to afford 5-diphenylmethyl-2',3',5'-tris-O-((1,1-dimethylethyl) dimethylsilyl)uridine as a colourless foam (5.94 g).

$^1$HNMR δ (CDCl$_3$): 8.49(bs, 1H), 7.35–7.0(m, 11H), 6.68(s, 1H), 5.76(d, 1H), 5.41(s, 1H), 3.87(m, 2H), 3.73(m, 1H), 3.29(dd, 1H), 3.21(dd, 1H), 0.85(m, 27H), 0.00(m, 18H).

(ii) The product of step (i) (6.9 g) was dissolved in dry pyridine (180 ml) under a atmosphere of nitrogen and treated with phosphorous pentasulphide (10.16 g) before refluxing for 20 hours. The solvent was removed under reduced pressure and the residue was partitioned between a saturated sodium bicarbonate solution and ethyl acetate. The organic phase was collected and solvent was removed under reduced pressure. The residue was purified by flash silica-gel chromatography eluting with ethyl acetate/iso-hexane mixtures to afford 5-diphenylmethyl-2',3',5'-tris-O-((1,1-dimethylethyl)dimethylsilyl)-4-thiouridine as a yellow foam (5.5 g).

MS: ESI+loop: 770(M+1).

(iii) The product of step (ii) (5.5 g) was treated with 1M tetra-n-butylammonium fluoride in tetrahydrofuran (21.5 ml) at room temperature. After stirring for 2 hours the solvent was removed under reduced pressure and the residue was purified by flash silica-gel chromatography eluting with ethyl acetate/iso-hexane mixtures to afford 5-diphenylmethyl-4-thiouridine as a yellow solid (1.3 g).

MS: EI: 426(M$^+$).

(iv) The trisodium salt of 5-diphenylmethyl-4-thiouridine-5'-(tetrahydrogen triphosphate)-P$^3$-monomethyl ester was prepared from the product of step (iii) according to the method of Example 24 steps (ii) and (iii).

$^{31}$P NMR δ (D$_2$O): −8.02(d), −10.15(d), −21.39(t).
MS: ESI+loop: 745(M+1).

Example 29

The triammonium salt of 5-(1,1-bis(4-methoxyphenyl)methyl)uridine-5'-(tetrahydrogen-triphosphate)-P$^3$-monomethyl ester (i) 5-(Hydroxy-1,1-bis(4-methoxyphenyl)methyl)-2',3',5'-tris-O-((1,1-dimethylethyl)dimethylsilyl)uridine was prepared from 2',3',5'-tris-O-((1,1-dimethylethyl)dimethylsilyl) uridine according to the method of Example 1 step (i) (but using 4,4'-dimethoxybenzophenone instead of benzophenone).

MS: FAB: m/e 811 (M+H—H$_2$O)$^+$.

(ii) The product of step (i) (3.8 g) was dissolved in dichloromethane (75 ml) and triethylsilane (0.8 ml) and was treated with trifluoroacetic acid(3.59 ml). After stirring for 1 hour at room temperature, the volatiles were removed under reduced pressure and any remaining traces removed by azeotroping four times with toluene. The residue was treated with 1M tetra-n-butylammonium fluoride solution in tetrahydrofuran (15 ml). After stirring for 36 hours, the solvent was removed under reduced pressure and the residue was purified by silica-gel chromatography eluting with 2% methanol in ethyl acetate to afford 5-(1,1-bis(4-methoxyphenyl)methyl)uridine as a white solid (1.4 g).

MS: FAB(+ve): m/e 471 (M+H)$^+$.

(iii) The triammonium salt of 5-(1,1-bis(4-methoxyphenyl)methyl)uridine 5'-(tetrahydrogen triphosphate)P$^3$-monomethyl ester was prepared from the product of step (ii) according to the method of Example 24 steps (ii) and (iii), with further purification by reverse phase HPLC eluting with 10% methanol in 0.1% aqueous ammonium acetate solution, and obtained as a white solid.

$^{31}$P NMR: δ (D$_2$O): −8.1 (d), −10.2(d), −21.6(t).
MS: ESI–loop: 723(M−H).

Example 30

Diammonium salt of 5-(1,1-bis(4-methoxyphenyl) methyl)-4-thiouridine-5'-(tetrahydrogen triphosphate)-P$^3$-monomethyl ester (i) The product of Example 29 step (i) (3.93 g) was dissolved in dichloromethane (70 ml), triethylsilane (0.83 ml) and cooled to 0° C. The mixture was treated with boron trifluoride diethyl etherate (2.34 ml) in small portions. After 30 min the mixture was quenched with cold saturated sodium bicarbonate solution. The organic phase was collected, the solvent was evaporated under reduced pressure and the product was azeotroped with toluene. The residue was dissolved in dimethylformamide (20 ml) and treated with imidazole (1.28 g) and t-butyldimethylsilylchloride (1.43 g) for 72 hours. The reaction mixture was quenched with water and extracted three times with iso-hexane. The organic phase was washed with water, collected, dried over magnesium sulphate and the solvent was evaporated under reduced pressure to give 5-(1,1-bis(4-methoxyphenyl)methyl)-2',3',5'-tris-O-((1,1-dimethylethyl)dimethylsilyl)uridine as a yellow oil (3.9 g).

MS: FAB(+ve)m/e: 813(M+1), FAB(−ve)m/e: 811(M−1).

(ii) 5-(1,1-bis(4-methoxyphenyl)methyl)-2',3',5'-tris-O-((1,1-dimethylethyl)dimethylsilyl)-4-thiouridine was prepared from the product of step (i) according to the method of Example 28 step (ii) as a yellow foam.

MS: FAB(−ve)m/e: 827(M−1).

(iii) 5-(1,1-bis(4-methoxyphenyl)methyl)-4-thiouridine was prepared from the product of step (ii) according to the method of Example 28 step (iii) as a yellow solid.

MS: APCI: m/e: 487(M+1).

(iv) The diammonium salt of 5-(1,1-bis(4-methoxyphenyl)methyl)-4-thiouridine-5'-(tetrahydrogen triphosphate)P$^3$-monomethyl ester was prepared from the product of step (iii) according to the method of Example 24 steps (ii) and (iii), purified by reverse phase HPLC eluting with 10% methanol in 0.1% aqueous ammonium acetate solution, and obtained as a yellow solid.

$^{31}$P NMR: δ (D$_2$O): −8.3(d), −10.3(d), −21.4(t).
MS: ESI(−ve)m/e: 739(M−H).

Example 31

Tri-n-butylammonium salt of 5-(1,1-bis(4-methoxyphenyl)methyl)-4-thiouridine-5'-(dihydrogen-phosphate)-monomethyl ester Obtained as a yellow solid from the products of Example 30 step (iv) by reverse phase HPLC purification of the final reaction mixture eluting with 10–50% aqueous methanol.

$^{31}$P NMR: δ (D$_2$O): 2.86(s).
MS: (FAB)(−ve): 579(M−1).

Example 32

Trisodium salt of 5-(9H-fluoren-9-yl)uridine-5'-(tetrahydrogen-triphosphate)-P³-monomethyl ester (i) 5-(9-Hydroxyfluoren-9-yl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using 9-fluorenone instead of benzophenone) as a colourless foam.

MS: FAB: m/e: 854/852(M+Rb).

(ii) The product of step (i) (6.56 g) was treated with a 1M solution of tetra-n-butyl ammonium fluoride in tetrahydrofuran (28.2 ml) and the mixture was stirred at room temperature for 16 hours. The solvent was evaporated under reduced pressure and the residue was purified by flash chromatography on silica-gel eluting with 10% methanol in ethyl acetate to give 5-(9-hydroxyfluoren-9-yl)uridine as a pale yellow solid (3.43 g).

MS: FAB: m/e: 425(M+1).

(iii) The product of step (ii) (3.37 g) was dissolved in dichloromethane (100 ml) and triethylsilane (1.39 ml) and treated with trifluoroacetic acid (6.23 ml). The mixture was stirred at room temperature for 36 hours. The solvent was evaporated under reduced pressure and the residue azeotroped three times with toluene. The remaining residue was purified by flash chromatography on silica-gel eluting with 15% methanol in ethyl acetate to give 5-(9H-fluoren-9-yl)uridine as white powder (1.09 g).

MS: FAB: m/e: 409(M+1).

(iv) The trisodium salt of 5-(9H-fluoren-9-yl)uridine-5'-(tetrahydrogen triphosphate)P³-monomethyl was prepared as a white powder from the product of step (iii) according to the method of Example 24 steps (ii) and (iii).

$^{31}$P NMR: δ (D$_2$O): −8.38(d), −10.46(d), −21.85(t).

MS: ESI−loop: m/e: 661(M−H).

Example 33

Disodium salt of 5-(9H-fluoren-9-yl)-4-thiouridine-5'-(tetrahydrogen-triphosphate)-P³-monomethyl ester (i) 5-(9H-fluoren-9-yl)-2',3',5'-tris-O-((1,1-dimethylethyl)dimethylsilyl)uridine was prepared from the product of Example 32 step (i) according to the method of Example 30 step (i) as a colourless foam and used directly in the next step.

(ii) 5-(9H-fluoren-9-yl)-2',3',5'-tris-O-((1,1-dimethylethyl)dimethylsilyl)-4-thiouridine was prepared from the product of step (i) according to the method of Example 28 step (ii) as a yellow foam.

MS: FAB(−ve): m/e: 765(M−1).

(iii) 5-(9H-fluoren-9-yl)-4-thiouridine was prepared from the product of step (ii) according to the method of Example 32 step (iii) as a yellow solid.

MS: EI: 424(M⁺).

(iv) The disodium salt of 5-(9H-fluoren-9-yl)-4-thiouridine-5'-(tetrahydrogen triphosphate)P³-monomethyl ester was prepared from the product of step (iii) according to the method of Example 24 steps (ii) and (iii) as a yellow powder.

$^{31}$P NMR: δ (D$_2$O): −8.95(d×2), −11.0(d×2), −22.3(t×2); -rotamers.

MS: FAB(+ve): 745(M+1).

Example 34

Diammonium salt of 5-(9H-fluoren-9-yl)-4-thiouridine-5'-(trihydrogen-diphosphate)-P³-monomethyl ester Obtained as a yellow solid from the products of Example 33 step (iv) by HPLC purification of the final reaction mixture but eluting with 10–50% methanol in 0.1% aqueous ammonium acetate solution instead.

$^{31}$P NMR: δ (D$_2$O): −8.2(d), −10.1(d).

MS: (FAB)(−ve): 597(M−1).

Example 35

Ammonium salt of 5-(9H-fluoren-9-yl)-4-thiouridine-5'-(dihydrogen-phosphate)-P³monomethyl ester Obtained from the products of Example 33 step (iv) by HPLC purification of the final reaction mixture as a yellow solid but eluting with 10–50% methanol in 0.1% aqueous ammonium acetate solution instead.

$^{31}$P NMR: δ (D$_2$O): 3.08(s), 2.75(bs)-rotamers.

MS: FAB(+ve): 519(M+1), FAB(−ve): 517(M−1).

Example 36

Trisodium salt of 5-triphenylsilyluridine-5'-(tetrahydrogen-triphosphate)-P³-monomethyl ester (i) 5-Triphenylsilyl-2',3',5'-tris-O-((1,1-dimethylethyl)dimethylsilyl)uridine was prepared as a colourless foam from 2',3',5'-tris-O-((1,1-dimethylethyl)dimethylsilyl)uridine according to the method of Example 1 step (i) (using triphenylsilylchloride instead of benzophenone).

MS: FAB(+ve): 845(M+1).

(ii) 5-triphenylsilyluridine was prepared from the product of step (i) according to the method of Example 28 step (iii).

MS: FAB(+ve): 503(M+1).

(iii) The trisodium salt of 5-triphenylsilyluridine-5'(tetrahydrogen triphosphate)-P³-monomethyl ester was prepared from the product of step (ii) according to the method of Example 24 steps (ii) and (iii) as a white powder.

$^{31}$P NMR: δ (D$_2$O): −8.12(d), −10.18(d), −21.55(t).

MS: (FAB): 823(M+1).

Example 37

Trisodium salt of 5-phenylthiouridine-5'-(tetrahydrogen-triphosphate)-P³-monomethyl ester (i) 5-phenylthiouridine (2.0 g) (for preparation see Tetrahedron Letters, (1987), 28, (1), 87–90) and 1,8-bis(dimethylamino)naphthalene (1.7 g) in dry trimethylphosphate (30 ml) were cooled to 0–5° C. under a nitrogen atmosphere. Phosphorous oxychloride (0.64 ml) was added dropwise and the resulting mixture stirred at low temperature for 3 hours before addition of bis(tributylammonium) pyrophosphate (50 ml of a 0.5M solution in dimethylformamide) and tri-n-butylamine (5.9 ml). After 5 minutes the reaction was quenched by addition of aqueous triethylammonium bicarbonate solution (300 ml of a 0.2M solution) and stirred for 15 minutes before being extracted three times with ethyl acetate (100 ml). The aqueous phase was concentrated under reduced pressure to approximately 80 ml and the residue purified by ion-exchange chromatography (DEAE Sephadex eluting with 0 –0.5M triethylammonium bicarbonate solution). The fractions containing the tetrakistriethylammonium salt of 5-phenylthiouridine-5'-triphosphate were pooled and lyophilised to leave a colourless gum (1.6 g).

$^{31}$P NMR: δ (D$_2$O): 4.8(d), −10.0(d), −21.0(t).

(ii) The product of step (i) (1.6 g) was dissolved in dry pyridine (30 ml) and concentrated to dryness under reduced pressure three times and then dissolved in dry pyridine (20 ml) and tri-n-octylamine (1.4 ml) and again this was evaporated to dryness under reduced pressure. The resulting gum was slurried in dry 1,4-dioxane (30 ml) under a nitrogen atmosphere and then treated with tri-n-butylamine (0.77 ml) and diphenylphosphochloridate (0.49 ml) with further stirring at room temperature for 2.5 hours. The solvents were then evaporated under reduced pressure. Dry diethyl ether (50 ml) and iso-hexane (200 ml) were added and the mixture was cooled to 0° C. under nitrogen atmosphere with stirring for 30 minutes. The supernatant was decanted and the remaining gum dissolved in 1,4-dioxane (10 ml) and then evaporated to dryness under reduced pressure. The resulting gum was dissolved in dry pyridine (15 ml) under a nitrogen atmosphere and treated with dry methanol (7.5 ml) and the resulting solution was stirred at room temperature for 2.5 hours. The volatiles were then removed by evaporation under reduced pressure and the remaining residue partitioned between water (50 ml) and diethyl ether (50 ml). The aqueous phase containing the product was purified by reverse phase chromatography (C-18 Sep-pak silica, eluting with water). The fractions containing the product were pooled and lyophilised and the residue was dissolved in water and passed down an ion-exchange column (Dowex-50 $Na^+$ form). The UV (254 nm) active fractions were pooled and lyophilised and the residue was purified by reverse phase chromatography (C18 Sep-pak silica, eluting with water). The fractions containing product were pooled and lyophilised to leave the trisodium salt of 5-phenylthiouridine-5'-(tetrahydrogen triphosphate)$P^3$-monomethyl ester as a white powder (0.3 g).

$^{31}$P NMR δ ($D_2O$): −8.2 (d), −10.2 (d), −21.6 (t).

MS: m/e 673 (M+H)$^+$.

Example 38

Trisodium salt of 5-ethyl-4-thiouridine-5'-(tetrahydrogen-triphosphate)-$P^3$-monomethyl ester (i) To a solution of 5-ethyl-2',3',5'-tris-O-benzoyluridine (0.58 g) in pyridine (18 ml) was added phosphorous pentasulphide (1.11 g) and then water (1.5 ml) dropwise. The resultant solution was heated at reflux for 16 hours. After cooling to room temperature the reaction mixture was concentrated to two thirds volume under reduced pressure and then treated with water (200 ml). After stirring for 1 hour the solid precipitate was filtered and dissolved in dichloromethane and again filtered. The mother liquor was collected, solvent removed under reduced pressure and the resulting solid filtered by washing three times with water (20 ml). The solid collected was further purified by silica-gel chromatography eluting with chloroform-methanol mixtures to leave 5-ethyl-2',3',5'-tris-O-benzoyl-4-thiouridine as a yellow solid (0.47 g).

MS: m/e 601 (M+H)$^+$.

(ii) Sodium hydride (0.1 g) (60% dispersion in mineral oil) was added to dry methanol (50 ml) under an atmosphere of nitrogen at 0° C. The product from step (i) (3.0 g) was added to the above solution and the whole was refluxed for 2 hours. After cooling to room temperature, glacial acetic acid (0.28 ml) was added and the volatiles were then removed under reduced pressure. The residue was dissolved in water (20 ml) and then extracted three times with diethyl ether (20 ml). The aqueous phase was evaporated to dryness under reduced pressure. The resulting solid was triturated with acetone and filtered to leave 5-ethyl-4-thiouridine as a yellow solid (1.39 g).

MS: m/e 289 (M+H)$^+$.

(iii) The tri sodium salt of 5-ethyl-4-thiouridine-5'-(tetrahydrogen triphosphate)-$P^3$-monomethyl ester was pre-pared from the product of step (ii) according to the method of Example 37 steps (i) and (ii) as a yellow powder.

$^{31}$ P NMR: δ ($D_2O$): −8.27(d), −10.44(d), −21.74(t).

MS: m/e 609 (M+H)$^+$.

Example 39

Trisodium salt of 5-((4-methoxy)phenylthio)uridine-5'-(tetrahydrogen triphosphate)-$P^3$-monomethyl ester (i) A suspension of dry lithium chloride (1.23 g) and palladium dichloride (2.55 g) was stirred under a nitrogen atmosphere in dry methanol for 14 hours forming a dark tan solution. 5-Chloromercuriuridine (3.44 g) (see JOC 1991, 56, (19), 5598 for preparation) and (4-methoxy) phenyldisulphide (5.00 g) were added and the mixture was stirred at room temperature for a further 14 hours. The mixture was saturated with hydrogen sulphide by bubbling the gas through the mixture for five minutes. The precipitate formed was filtered through celite and further washed with methanol. The mother liquor was absorbed onto silica-gel and subjected to flash chromatography eluting with 10% methanol in dichloromethane to give a white semi-solid upon evaporation of the product fractions. This was dissolved in methanol and filtered and again the solvent was removed in vacuo leaving 5-((4-methoxy)phenylthio) uridine as a white solid (2.43 g).

MS: FAB: m/e 383 (M+H)$^+$.

(ii) The tetrakistriethylammonium salt of 5-((4-methoxy) phenylthio)uridine-5'-triphosphate was prepared from the product of step (i) according to the method of Example 37 step (i) as a white powder.

$^{31}$P NMR: δ ($D_2O$): −6.46 (d), −10.17 (d), −21.40 (t).

(iii) The trisodium salt of 5-((4-methoxy)phenylthio) uridine-5'-(tetrahydrogen-triphosphate)-$P^3$-monomethyl ester was prepared from the product of step (ii) according to the method of Example 37 step (ii) as a white powder.

$^{31}$P NMR: δ ($D_2O$): −8.21 (d), −10.26 (d), −21.64 (t).

MS: m/e 635 (M−3$Na^+$ +2H).

Example 40

Trisodium salt of 5-((2-phenyl)phenylthio)uridine-5'-(tetrahydrogen-triphosphate)-$P^3$-monomethyl ester (i) To a solution of 2-bromo-biphenyl (10.6 g) in dry THF (150 ml) under an atmosphere of nitrogen at −78° C. was added 53.5 ml of a 1.7M solution of t-butyllithium in pentane dropwise over 15 minutes using a dropping funnel. A deep yellow solution was formed. After 30 minutes the reaction mixture was allowed to reach and remain at room temperature for five minutes by removing the cooling bath. The reaction mixture was then cooled to approximately −10° C. and quenched with solid sulphur (1.45 g). The mixture was then allowed to reach room temperature with further stirring for 1 hour. The mixture was carefully quenched with saturated aqueous ammonium chloride solution (100 ml) and then extracted with diethyl ether. The aqueous phase was collected, acidified with 2M hydrochloric acid and extracted with diethyl ether. The organic phase was collected and the solvent removed in vacuo leaving the thiol as a colourless oil (7.8 g). The crude thiol was dissolved in dimethylsulphoxide (4 ml) and stirred at room temperature for 24 hours and then at 60–80° C. for a further 24 hours. The cooled mixture was partitioned between diethyl ether and 1M sodium hydroxide solution. The organic phase was collected and the solvent was removed in vacuo. The resulting oil was purified by flash chromatography on silica-gel eluting with 10% diethyl ether in isohexane to give 2-(phenyl)phenyldisulphide as a pale yellow gum (6.9 g).

$^1$H NMR: δ (CDCl$_3$): 7.2–7.6 (m, aromatics).

MS: ESI: m/e 370 (M+H)$^+$.

(ii) 5-((2-Phenyl)phenylthio)uridine was prepared from the product of step (i) and 5-chloromercuriuridine according to the method of Example 39 step (i) as a colourless solid.

MS: FAB (+ve): m/e 429 (M+H)$^+$.

(iii) The trisodium salt of 5-((2-phenyl)phenylthio) uridine-5'-(tetrahydrogen-triphosphate)-P$^3$-monomethyl ester was prepared from the product of step (ii) according to the method of Example 24 steps (ii) and (iii) as a colourless solid.

$^{31}$P NMR: δ (D$_2$O): −7.95 (d), −10.04 (d), −21.24 (t).

MS: ESI (loop): 725 (M−3H+2Na$^+$).

Example 41

Trisodium salt of $^5$-((3-phenyl)phenylthio)uridine-5'-(tetrahydrogen-triphosphate)-P$^3$-monomethyl ester (i) 3-(Phenyl)phenyldisulphide was prepared from 3-bromo-biphenyl according to the method of Example 40 step (i) as a white solid.

MS: ESI: m/e 370(M+H)$^+$.

(ii) 5-((3-Phenyl)phenylthio)uridine was prepared from the product of step (i) and 5-chloromercuriuridine according to the method of Example 40 step (ii) as a colourless solid.

MS: FAB (+ve): m/e 429(M+H)$^+$.

(iii) The trisodium salt of 5-((3-phenyl)phenylthio) uridine-5'-(tetrahydrogen triphosphate)-P$^3$-monomethyl ester was prepared from the product of step (ii) according to the method of Example 24 steps (ii) and (iii) as a white powder.

$^{31}$P NMR: δ (D$_2$O): −8.23(d), −10.21(d), −21.50(t).

MS: ESI (loop): 725 (M−3H+2Na$^+$).

Example 42

Trisodium salt of 5-((4-phenyl)phenylthio)uridine-5'-(tetrahydrogen-triphosphate)-P$^3$-monomethyl ester (i) 4-(Phenyl)phenyldisulphide (J. Chem. Soc. P1: 1987, (1), 187) was prepared from 4-bromo-biphenyl according to the method of Example 40 step (i) as a white solid.

MS: ESI: m/e 370(M+H)$^+$.

(ii) 5-((4-Phenyl)phenylthio)uridine was prepared from the product of step (i) and 5-chloromercuriuridine according to the method of Example 40 step (ii) as a white solid.

MS: FAB (−ve): m/e 427(M−H)$^+$.

(iii) The trisodium salt of 5-((4-phenyl)phenylthio) uridine-5'-(tetrahydrogen-triphosphate)-P$^3$-monomethyl ester was prepared from the product of step (ii) according to the method of Example 24 steps (ii) and (iii) as a white powder.

$^{31}$P NMR: δ (D$_2$O): −8.14(d), −10.17(d), −21.57(t).

MS:ESI (loop): 681 (M−3Na$^+$—H).

Example 43

Triammonium salt of 5-(2-naphthylthio)uridine-5'-(tetrahydrogen-triphosphate)-P$^3$-monomethyl ester (i) 5-(2-Naphthylthio)uridine was prepared from 5-chloromercuriuridine and 2,2'-dinaphthyl disulphide (see Synth. Commun. 1985, 15, (1), 1 for preparation) according to the method of Example 40 step (ii).

MS: FAB: m/e 409 (M+Li)$^+$.

(ii) The triammonium salt of 5-(2-naphthylthio)uridine-5'-(tetrahydrogen-triphosphate)-P$^3$-monomethyl ester was prepared as a white solid from the product of step (i) according to the method of Example 24 steps (ii) and (iii), and purified by reverse phase HPLC using a 10–60% methanol in 0.5% aqueous ammonium acetate mixture as eluant.

$^{31}$P NMR: δ (D$_2$O): −8.19(d), −10.22(d), −21.50(t).

Example 44

Trisodium salt of 5-((3-phenoxy)phenylmethyl)-4-thiouridine-,'-(tetrahydrogen-triphosphate)-P$^3$-monomethyl ester (i) 5-(Hydroxy-((3-phenoxy)phenyl)methyl)-2',3',5'-tris-O-((1,1-dimethylethyl)dimethylsilyl)uridine was prepared from 2',3',5'-tris-O-((1,1-dimethylethyl)dimethylsilyl) uridine according to the method of Example 1 step (i) (using 3-phenoxybenzaldehyde instead of benzophenone) as a colourless foam.

MS: ESI(+ve): 785(M+1).

(ii) 5-((3-Phenoxy)phenylmethyl)-2',3',5'-tris-O-((1,1-dimethylethyl)dimethylsilyl)uridine was prepared from the product of step (i) according to the method of Example 40 step (i) as a colourless foam.

MS: ESI(+ve): 769(M+1).

(iii) 5-((3-Phenoxy)phenylmethyl)-2',3',5'-tris-O-((1,1-dimethylethyl)dimethylsilyl)-4-thiouridine was prepared from the product of step (ii) according to the method of Example 28 step (ii) as a yellow foam.

MS: FAB(−ve): 783(M−1).

(iv) The product of step (iii) (3.5 g) was dissolved in acetonitrile (70 ml) and treated with a 1:1 hydrofluoric acid-pyridine complex (20 ml). After 3 hours the mixture was quenched with saturated aqueous sodium carbonate solution (100 ml) and the product extracted into ethyl acetate. The organic phase was collected, dried over magnesium sulphate and the solvent was removed under reduced pressure. The residue was purified by flash silica-gel chromatography eluting with chloroform-methanol mixtures to afford 5-((3-phenoxy)phenylmethyl)-4-thiouridine as a yellow powder (1.5 g).

MS: FAB(+ve): 443(M+1), FAB(−ve): 441(M−1).

(v) The trisodium salt of 5-((3-phenoxy)phenylmethyl)-4-thiouridine-5'-(tetrahydrogen-triphosphate)-P$^3$-monomethyl ester was prepared from the product of step (iv) according to the method of Example 24 steps (ii) and (iii) as yellow powder.

$^{31}$P NMR: δ (D$_2$O): −8.16(d), −10.35(d), −21.56(t).

MS: FAB: m/e 763 (M+H)$^+$.

Example 45

Trisodium salt of 5-((4-phenoxy)phenylmethyl)-4-thiouridine-5'-(tetrahydrogen-triphosphate)-P$^3$-monomethyl ester (i) 5-(Hydroxy-((4-phenoxy)phenyl)methyl)-2',3',5'-tris-O-((1,1-dimethylethyl-dimethylsilyl)uridine was prepared from 2',3',5'-tris-O-((1,1-dimethylethyl)dimethylsilyl) uridine according to the method of Example 1 step (i) (using 4-phenoxybenzaldehyde instead of benzophenone) as a colourless foam.

MS: FAB(+ve): 883(M+Rb).

(ii) 5-((4-Phenoxy)phenylmethyl)-2',3',5'-tris-O-((1,1-dimethylethyl)dimethylsilyl)uridine was prepared from the product of step (i) according to the method of Example 28 step (i) as a colourless foam.

MS: FAB(+ve): 769(M+1), 853(M+Rb).

(iii) 5-((4-Phenoxy)phenylmethyl)-2',3',5'-tris-O-((1,1-dimethylethyl)dimethylsilyl)-4-thiouridine was prepared from the product of step (ii) according to the method of Example 28 step (ii) as a yellow foam.

MS: FAB(−ve): 783(M−1).

(iv) 5-((4-Phenoxy)phenylmethyl)-4-thiouridine was prepared from the product of step (iii) according to the method of Example 30 step (i) as a yellow solid.

MS: FAB(+ve): 443(M+1).

(v) The trisodium salt of 5-((4-phenoxy)phenylmethyl)-4-thiouridine-5'-(tetrahydrogen-triphosphate)-$P^3$-monomethyl ester was prepared from the product of step (iv) according to the method of Example 24 steps (ii) and (iii) as a yellow solid.

$^{31}$P NMR: δ ($D_2O$): −8.0(d), −10.25(d), −21.5(t).

MS: ESI(−ve): m/e 695 (M−2Na+2H).

Example 46

Trisodium salt of 5-((3-phenylmethyloxy)phenylmethyl)-4-thiouridine-5'-(tetrahydrogen-triphosphate)-$P^3$-monomethyl ester (i) 5-(Hydroxy-((3-phenylmethoxy)phenyl)methyl)-2',3',5'-tris-O-((1,1-dimethylethyl)dimethylsilyl)uridine was prepared from 2',3',5'-tris-O-((1,1-dimethylethyl)dimethylsilyl) uridine according to the method of Example 1 step (i) (using 3-phenylmethyloxybenzaldehyde instead of benzophenone) as a colourless foam.

MS: FAB(−ve): 797(M−1).

(ii) 5-((3-Phenylmethoxy)phenylmethyl)-2',3',5'-tris-O-((1,1-dimethylethyl)dimethylsilyl)uridine was prepared from the product of step (i) according to the method of Example 30 step (i) as a colourless foam.

MS: FAB(−ve): 781(M−1).

(iii) 5-((3-Phenylmethoxy)phenylmethyl)-2',3',5'-tris-O-((1,1-dimethylethyl)dimethylsilyl)-4-thiouridine was prepared from the product of step (ii) according to the method of Example 28 step (ii) as a yellow foam.

MS: FAB(−ve): 797(M−1).

(iv) 5-((3-Phenylmethoxy)phenylmethyl)-4-thiouridine was prepared from the product of step (iii) according to the method of Example 44 step (iv) as a yellow solid.

MS: ESI: 457(M+1).

(v) The trisodium salt of 5-((3-henylmethoxy)phenylmethyl)-4-thiouridine-5'-(tetrahydrogen triphosphate)-$P^3$-monomethyl ester was prepared from the product of step (iv) according to the method of Example 24 steps (ii) and (iii) as a yellow solid.

$^{31}$P NMR: δ ($D_2O$): −8.12(d), −10.33(d), −21.55(t).

MS: FAB(+ve): 777(M+1).

Example 47

Trisodium salt of 5-((4-phenylmethoxy)phenylmethyl)-4-thiouridine-5'-(tetrahydrogen-triphosphate)-$P^3$-monomethyl ester (i) 5-(Hydroxy-((4-phenylmethoxy)phenyl)methyl)-2',3',5'-tris-O-((1,1-dimethylethyl)dimethylsilyl)uridine was prepared from 2',3',5'-tris-O-((1,1-(dimethylethyl)dimethylsilyl)uridine according to the method of Example 1 step (i) (using 4-phenylmethyloxybenzaldehyde instead of benzophenone) as a colourless foam.

MS: FAB(+ve): 883(M+Rb).

(ii) 5-((4-Phenylmethoxy)phenylmethyl)-2',3',5'-tris-O-((1,1-dimethylethyl)dimethylsilyl)uridine was prepared from the product of step (i) according to the method of Example 28 step (i) as a colourless foam.

MS: FAB(+ve): 769(M+1), 853(M+Rb).

(iii) 5-((4-Phenylmethoxy)phenylmethyl)-2',3',5'-tris-O-((1,1-dimethylethyl)dimethylsilyl)-4-thiouridine was prepared from the product of step (ii) according to the method of Example 28 step (ii) as a yellow foam.

MS: FAB(−ve): 797(M−1).

(iv) 5-((4-Phenylmethoxy)phenylmethyl)-4-thiouridine was prepared from the product of step (ii) according to the method of Example 30 step (ii) as a yellow solid.

MS: FAB(+ve): 457(M+1).

(v) The trisodium salt of 5-((4-Phenylmethyloxy)phenylmethyl)-4-thiouridine-5'-(tetrahydrogen triphosphate)-$P^3$-monomethyl ester was prepared from the product of step (iv) according to the method of Example 24 steps (ii) and (iii) as a yellow solid.

$^{31}$P NMR: δ ($D_2O$): −8.0(d), −10.15(d), −21.5(t).

MS: ESI(−ve): 709(M−2Na+2H).

Example 48

Trisodium salt of 5-(4-(1,1-dimethylethyl)phenylmethyl)-4-thiouridine-5'-(tetrahydrogen-triphosphate)-$P^3$-monomethyl ester.

(i) 5-((4-(1,1-Dimethylethyl)phenyl)hydroxymethyl)-2',3',5'-tris-O-((1,1-dimethylethyl)dimethylsilyl)uridine was prepared from 2',3',5'-tris-O-((1,1-dimethylethyl)dimethylsilyl)uridine according to the method of Example 1 step (i) (using 4-(1,1-dimethylethyl)benzaldehyde instead of benzophenone) as a colourless foam.

$^1$H NMR: δ ($CDCl_3$): 8.13(s,1H), 7.44(s,1H), 7.15–7.45 (m,4H), 5.84(d, 1H), 5.80(d, 1H), 5.5(d, 1H), 4.57(d, 1H), 4.10(m,1H), 3.98(m, 2H), 3.73(m, 1H), 3.60(m, 1H), 3.17(d, 1H), 3.13(d, 1H), 1.23(s, 9H), 0.81(s, 9H), 0.76(s, 9H), −0.15–0.05(m, 18H).

(ii) 5-(4-(1,1-Dimethylethyl)phenylmethyl)-2',3',5'-tris-O-((1,1-dimethylethyl)dimethylsilyl)uridine was prepared from the product of step (i) according to the method of Example 30 step (i).

$^1$H NMR: δ ($CDCl_3$): 8.04(s,1H), 7.3(s,1H), 7.17(d,2H), 7.04(d, 2H), 5.85(d, 1H), 4.03(m, 1H), 3.93(m,2H), 3.73(dd, 1H), 3.6(dd, 1H), 3.51(d, 2H), 1.2(s, 9H), 0.8(m, 27H), −0.2–0.0(m, 18H).

(iii) 5-(4-(1,1-Dimethylethyl)phenylmethyl)-2',3',5'-tris-O-((1,1-dimethylethyl)dimethylsilyl)-4-thiouridine was prepared from the product of step (ii) according to the method of Example 28 step (ii). 1H NMR: δ ($CDCl_3$): 9.38(s, 1H), 7.28(s, 1H), 7.19(d,2H), 7.05(d, 2H), 5.79(d, 1H), 4.06(dd, 1H), 3.95(m, 2H), 3.86(d, 1H), 3.77(d, 1H), 3.73(dd,1H), 3.58(dd, 1H), 1.2(s, 9H), 0.81 (s, 9H), 0.78(s, 9H), −0.15–0.00(m, 18H).

(iv) 5-(4-(1,1-Dimethylethyl)phenylmethyl)-4-thiouridine was prepared from the product of step (iii) according to the method of Example 28 step (iii).

$^1$H NMR: δ ($CDCl_3$): 11.15(s,1H), 7.35(s,1H), 7.16(s, 1H), 7.15(d,2H), 5.73(d, 1H), 4.65(bs, 1H), 4.23(m, 1H), 4.13(bs, 2H), 4.95–4.05(bs, 1H), 3.81 (d, 1H), 3.74(d, 1H), 3.5(bs, 2H), 1.3(s, 9H).

39

(v) The trisodium salt of 5-(4-(1,1-dimethylethyl) phenylmethyl)-4-thiouridine-5'-(tetrahydrogen-triphosphate)-P$^3$-monomethyl ester was prepared from the product of step (iv) according to the method of Example 24 steps (ii) and (iii) as a yellow solid.

$^{31}$P NMR: δ (D$_2$O): −8.3(d), −10.7(d), −21.76(t).
MS: ESI-loop: 659.

Example 49

Sodium salt of 5-(4-(1,1-dimethylethyl) phenylmethyl)-4-thiouridine-5'-(dihydrogen-phosphate) monomethyl ester Obtained from the products of Example 48 step (v) by reverse phase HPLC purification of the final reaction mixture as a yellow solid using 10–50% methanol in 1% aqueous ammonium acetate solution.

$^{31}$ P NMR: δ (D$_2$O): 3.077(s).
MS: FAB(+ve): 523(M+1).

Example 50

Trisodium salt of 5-((3-methoxy-4-phenylmethyloxy)phenylmethyl)-4-thiouridine-5'-(tetrahydrogen-triphosphate)-P$^3$-monomethyl ester (i) 5-(Hydroxy-((3-methoxy-4-phenylmethoxy)phenyl)methyl)-2',3',5'-tris-O-((1,1-dimethylethyl)dimethylsilyl) uridine was prepared from 2',3',5'-tris-O-((1,1-dimethylethyl)dimethylsilyl)uridine according to the method of Example 1 step (i) (using 3-methoxy-4-phenylmethyloxybenzaldehyde instead of benzophenone) as a colourless foam.

$^1$H NMR: δ (CDCl$_3$): 8.3(bs,1H), 7.2–7.45(m,6H), 6.94 (bs,1H), 6.80(m,2H), 5.85(2d), 5.45(d, 1H), 5.07(s, 2H), 4.03(m, 1H), 3.93(m, 2H), 3.8(s, 3H), 3.68(m, 1H), 3.58(m, 1H), 3.24(d, 1H), 0.82(s, 9H), 0.81(s, 9H), 0.76(s, 9H), −0.15–0.0(m, 18H).

(ii) 5-((3-Methoxy-4-phenylmethoxy)phenylmethyl)-2', 3',5'-tris-O-((1,1-dimethylethyl)dimethylsilyl)uridine was prepared from the product of step (i) according to the method of Example 28 step (i).

$^1$H NMR: δ (CDCl$_3$): 8.27(bs,1H), 7.2–7.45(m,6H), 6.71 (s,1H), 6.67(d, 1H), 6.54(dd, 1H), 5.86(d, 1H), 5.02(s, 2H), 4.03(m, 1H), 3.98(m, 2H), 3.76(s, 3H), 3.71(dd, 1H), 3.64 (dd, 1H), 3.46(d, 1H), 3.51(d, 1H), 0.82(s, 9H), 0.81(s, 9H), 0.75(s, 9H), −0.2–0.0(m, 18H).

(iii) 5-((3-Methoxy-4-phenylmethoxy)phenylmethyl)-2', 3',5'-tris-O-((1,1-dimethylethyl)dimethylsilyl)-4-thiouridine was prepared from the product of step (ii) according to the method of Example 28 step (ii).

$^1$H NMR: δ (CDCl$_3$): 9.31 (s, 1H), 7.36(d,2H), 7.35–7.25 (m,3H), 7.23(d, 1H), 6.76(d, 1H), 6.7(d, 1H), 6.54(dd, 1H), 5.83(d, 1H), 5.05(s, 1H), 4.08(m, 1H), 3.98(m, 2H), 3.79(s, 3H), 3.78(m, 1H), 3.71(dd, 1H), 3.6(dd, 1H), 0.84(s, 9H), 0.83(s, 9H), 0.79(s, 9H), −0.2–0.05(m, 18H).

(iv) 5-((3-Methoxy-4-phenylmethoxy)phenylmethyl)-4-thiouridine was prepared from the product of step (iii) according to the method of Example 28 step (iii).

$^1$H NMR: δ (CDCl$_3$): 11.09(s, 1H), 7.25–7.5(m,5H), 7.14(s, 1H), 6.72–6.68(m, 1H), 5.66(d, 1H), 5.07(s, 2H), 4.67(bs, 1H), 4.23(m, 1H), 4.10(m, 2H), 4.00(s, 1H), 3.81(s, 3H), 3.70(m, 2H), 3.5(m, 2H).

(v) The trisodium salt of 5-((3-methoxy-4-phenylmethoxy)phenylmethyl)-4-thiouridine-5'-(tetrahydrogen-triphosphate)-P$^3$-monomethyl ester was prepared from the product of step (iv) according to the method of Example 24 steps (ii) and (iii) as a yellow solid.

$^{31}$P NMR: δ (D$_2$O): −8.24(d), −10.45(d), −21.7(t).
MS: FAB(+ve): 807(M+1).

Example 51

Disodium salt of 5-((3-methoxy-4-phenylmethoxy) phenylmethyl)-4-thiouridine-5'-(trihydrogen-diphosphate)-P$^3$-monomethyl ester Prepared from the products of Example 50 step (v) by reverse phase HPLC purification using 10–50% methanol in1% aqueous ammonium acetate solution followed by anion exchange chromatography (using Dowex-50 Na$^+$ form) and lyophilisation of the aqueous solution obtained to secure a yellow solid.

$^{31}$P NMR: δ (D$_2$O): −8.15(d), −10.2(d).
$^1$H NMR: δ (D$_2$O): 7.74(s, 1H), 7.4–7.2(m, 5H), 6.88(s, 1H), 6.78(d, 1H), 6.68(d, 1H), 5.77(d, 1H), 4.94(s, 2H), 4.25(m, 2H), 4.18(m, 1H), 4.10(m, 2H), 3.83(d, 1H), 3.73(d, 1H), 3.69(s, 3H), 3.41 (d, 3H).

PHARMACOLOGICAL DATA

Example A

The following example describes the assay used to determine how strongly the compounds of the invention bind to P2-purinoceptor 7-TM G-protein coupled receptors. The assay used a human P2Y2 receptor clone which was isolated from HL60 cells cDNA and then stably transfected into a Jurkat cell line (using methods described in "Cloning and Characterisation of a Bovine P$_{2Y}$ Receptor" Henderson et al (1995), 212, 2, 648–656; Parr et al Proc. Natl. Acad. Sci U.S.A. (1994), 91, 3275–3279 and Proc Natl Acad Sci U.S.A. (1994), 91, 13067). The cloned receptor mediates an increase in intracellular calcium in the cell line, which possesses no endogenous nucleotide receptor of its own.

The transfected Jurkat cells were maintained at a concentration of from about 1×10$^5$ to 10×10$^5$ cells/ml in RPMI containing 4% heat inactivated bovine serum, 2% penicillin/streptomycin and1% glutamine. The cells were incubated at 37° C. in an atmosphere of air with 5% CO$_2$.

The cells were spun down at 1000 r.p.m. for 5 minutes and resuspended in 10 ml basal salt solution (BSS) containing 125 mM of NaCl, 5 mM of KCl, 1mM of MgCl, 1.5 mM of CaCl$_2$, 25 mM of HEPES, 5 mM of glucose and 1 mg/ml of bovine serum albumin, having a pH of 7.3. The concentration of cells was determined using a Technicon cell counter. From 0.75×10$^8$ to 1×10$^8$ cells were spun down, resuspended to a concentration of 3.3×10$^7$ cells/ml in BSS and incubated with either 17 μM fluo-3AM or 17 μM Fura-2AM at 37° C. for 35 minutes with vigorous shaking. The dye used was dependent upon the fluorescence and absorption properties of the compounds of the invention. In general for compounds of formula (I) wherein Q$^1$ represents a S atom, fluo-3AM was used and for compounds wherein Q$^1$ represents an O atom, either fluo-3AM or fura-2AM were used. The cells were again spun down and washed once with the same volume of BSS before being resuspended in BSS to a concentration of 1×10$^6$ cells/ml ready for testing.

When fluo-3AM was used as the dye, the cell solution was left at room temperature to recover for approximately 30 minutes before testing. Fura-2AM loaded cells were divided into aliquots of about 10 ml and were warmed to 37° C. for 10 minutes before testing.

Calcium responses were measured on a SPEX Fluomax using 508 nm excitation and 525 nm emission wavelengths at room temperature for Fluo-3AM loaded cells and 340/380 nm excitation and 510 nm emission wavelengths for Fura-2AM loaded cells. Each cuvette contained 2 ml of cells and was stirred at high speed throughout the test. Basal fluorescence was measured for 5 seconds before 20 μl of a $10^{-2}$–$10^{-6}$M solution of the test compound in water was added to the 2 ml solution of the cells. The response was calibrated by the addition of Triton-X-100 (68 μl, 10% solution) and then EGTA (180 μl, 0.5 M solution). For each compound the response was compared to that of UTP.

The compounds exemplified have pA2 values greater than 4.0.

We claim:

1. A compound of formula (I) or salts thereof:

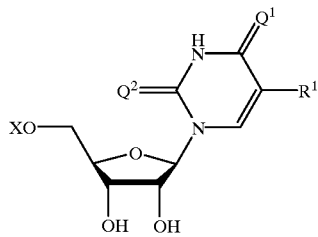

(I)

wherein X represents H or a group of formula (i), (ii) or (iii):

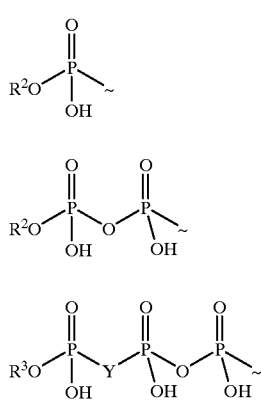

(i)

(ii)

(iii)

$R^1$ represents a $C_{1-6}$-alkyl, $C(R^4)_2R^5$, $CHR^6R^5$, $Si(R^4)_3$, $C(O)R^6$, or $SR^6$ group or $R^1$ represents a group of formula (iv) or (v):

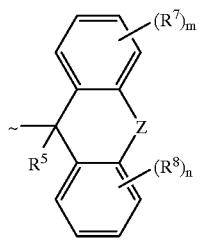

(iv)

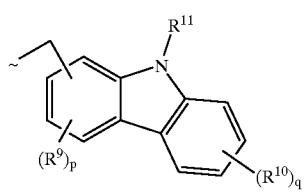

(v)

$R^2$ represents a hydrogen atom or methyl;

$R^3$ represents a hydrogen atom or a $C_{1-6}$ alkyl group which is optionally substituted by one or more $C_{1-6}$-alkoxy, $C_{1-6}$-alkylthio, $C_{3-8}$-cycloalkyl, or phenyl groups wherein the one or more phenyl groups are optionally substituted by one or more halogen atoms, hydroxy, $C_{1-4}$-alkyl or $C_{1-4}$-alkoxy groups;

$R^4$ represents phenyl optionally substituted by one or more halogen atoms, $C_{1-4}$-alkoxy, $C_{1-4}$-alkylthio or $C_{1-4}$-alkyl groups wherein the one or more alkyl groups are optionally substituted by one or more F atoms;

$R^5$ represents a hydrogen atom or a $C_{1-6}$-alkoxy, $C_{1-6}$-alkylthio, $C_{1-6}$-alkyl or a phenyl group;

$R^6$ represents a $C_{6-10}$-aryl group which is optionally substituted by one or more halogen atoms, $C_{6-10}$-aryl, $C_{6-10}$-aryloxy, $C_{3-10}$-cycloalkyl, $C_{1-6}$-alkylthio, $C_{1-6}$-alkyl or $C_{6-10}$-alkoxy groups, each of which substituents are optionally substituted by one or more halogen atoms, $C_{1-6}$-alkyl, phenyl or $C_{1-6}$-alkoxy groups;

$R^7$ and $R^8$ each independently represent a hydrogen; a halogen atom or a $C_{1-4}$-alkoxy, $C_{1-4}$-alkylthio or $C_{1-4}$-alkyl group wherein the one or more alkyl groups are optionally substituted by one or more F atoms;

$R^9$ and $R^{10}$ each independently represent a halogen atom or a $C_{1-4}$-alkoxy, $C_{1-4}$-alkylthio, $C_{1-4}$-alkyl optionally substituted by a phenyl group or a $C_{3-8}$-cycloalkyl group;

$R^{11}$ represents $C_{1-6}$-alkyl group optionally substituted by phenyl;

$Q^1$ and $Q^2$ each independently represent O or S;

Y represents O or a $CF_2$, $CCl_2$ or a $CBr_2$ moiety;

Z represents a direct bond, O, S, $(CH_2)_t$ wherein when t is greater than 1, one of the $CH_2$ moieties is optionally replaced by an O or S atom, $CH_2CH$=CH, $CH_2CH$=$CHCH_2$ or CH=CH;

n, m, p and q each independently represent 0 or an integer from 1 to 4;

t represents an integer from 1 to 4;

provided that:

(a) when X represents H then $Q^1$ represents a S atom and $R^1$ represents a group of formula (iv) where $R^5$ is hydrogen, and Z is $CH_2CH_2$ or CH=CH;

(b) when $R^3$ represents H then Y does not represent O;

(c) when X represents a group of formula (i) or (ii) then:

(i) $R^1$ represents a group of formula (iv) wherein Z represents a direct bond, O, CH=CH, or $CH_2CH_2$, and $R^7$, $R^8$, n and m are as defined above; or (ii) $R^1$ represents $C(R^4)_2R^5$ wherein $R^4$ represents phenyl substituted by one or more halogen atoms or one or more $C_{1-4}$-alkoxy, $C_{1-4}$-alkylthio and/or $C_{1-4}$-alkyl groups wherein the one or more alkyl groups are optionally substituted by one or more F atoms and $R^5$ represents a hydrogen atom; or (iii) $R^1$ represents $CHR^6R^5$ wherein $R^6$ represents a $C_{6-10}$-aryl group which is substituted by one or more halogen atoms or one or more $C_{6-10}$-aryl, $C_{6-10}$-aryloxy, $C_{6-10}$-arylthio, $C_{3-8}$-cycloalkyl, $C_{1-6}$-alkylthio, $C_{1-6}$-alkyl and/or $C_{1-6}$-alkoxy groups, each of which optional substituents are optionally substituted by one or more halogen atoms or one or more $C_{1-6}$-alkyl, phenyl or $C_{1-6}$-alkoxy groups and $R^5$ is as defined above but does not represent phenyl;

(d) when $R^1$ represents $C_{1-6}$-alkyl then $Q^1$ represents a S atom;

(e) when $R^1$ represents $CHR^5R^6$ then $R^1$ does not represent phenyl.

2. A compound according to claim 1 wherein X represents

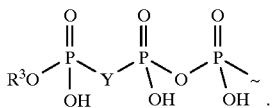

3. A compound according to claim 2 wherein Y represents $CF_2$, $CCl_2$, or $CBr_2$, and $R^3$ represents hydrogen.

4. A compound according to claim 1 wherein $R^1$ represents $C(R^4)_2R^5$ where $R^4$ represents phenyl substituted by one or more halogen atoms and one or more methyl groups and $R^5$ is hydrogen.

5. A compound according to claim 1 wherein $R^1$ represents

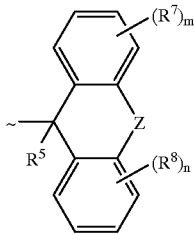

wherein $R^7$ and $R^8$ are hydrogen and Z is O, $(CH_2)_2$ or CH=CH.

6. A compound according to claim 1 wherein $Q^1$ represents a S atom.

7. A compound according to claim 1 which is:
monoanhydride of 5-diphenylmethyluridine-5'-phosphate with dichloromethylenebisphosphonic acid;
monoanhydride of 5-(9H-fluoren-9-yl)-4-thiouridine-5'-phosphate with dichloromethylenebisphosphonic acid;
monoanhydride of 5-(9H-xanthen-9-yl)-4-thiouridine-5'-phosphate with dichloromethylenebisphosphonic acid;
monoanhydride of 5-(5H-dibenzo[a,d]cyclohepten-5-yl)-4-thiouridine-5'-phosphate with dichloromethylenebisphosphonic acid;
5-(5H-Dibenzo[a,d]cyclohepten-5-yl)-4-thiouridine;
monoanhydride of 5-(10,11-dihydro-5H-dibenzo[a,d]cyclohepten-5-yl)-4-thiouridine-5'-phosphate with dichloromethylenebisphosphonic acid;
5-(10,11-dihydro-5H-dibenzo[a,d]cyclohepten-5-yl)-4-thiouridine;
monoanhydride of 5-(1,1-bis(4-methylphenyl)methyl)-4-thiouridine-5'-phosphate with dichloromethylenebisphosphonic acid;
monoanhydride of 5-(1,1-bis(4-chlorophenyl)methyl)-4-thiouridine-5'-phosphate with dichloromethylenebisphosphonic acid;
monoanhydride of 5-(1,1-bis(3,4-dichlorophenyl)methyl)-4-thiouridine-5'-phosphate with dichloromethylenebisphosphonic acid;
monoanhydride of 5-(1,1-bis(4-methoxyphenyl)methyl)-4-thiouridine-5'-phosphate with dichloromethylenebisphosphonic acid;
monoanhydride of 5-(3,6-dimethoxy-9H-fluoren-9-yl)-4-thiouridine-5'-phosphate with dichloromethylenebisphosphonic acid;
monoanhydride of 5-(3-(4-methylphenoxy)phenylmethyl)-4-thiouridine-5'-phosphate with dichloromethylenebisphosphonic acid;
monohydride of 5-(3-(4-chlorophenoxy)phenylmethyl)-4-thiouridine-5'-phosphate with dichloromethylenebisphosphonic acid;
monoanhydride of 5-(3-(3,4-dichlorophenoxy)phenylmethyl)-4-thiouridine-5'-phosphate with dichloromethylenebisphosphonic acid;
monoanhydride of 5-(3-(4-methoxyphenoxy)phenylmethyl)-4-thiouridine-5'-phosphate with dichloromethylenebisphosphonic acid;
monoanhydride of 5-((3-methoxy-4-phenylmethoxy)phenylmethyl)-4-thiouridine-5'-phosphate with dichloromethylenebisphosphonic acid;
monoanhydride of 5-((4-methoxy-3-phenylmethoxy)phenylmethyl)-4-thiouridine-5'-phosphate with dichloromethylenebisphosphonic acid;
monoanhydride of 5-(4-butoxyphenylmethyl)-4-thiouridine-5'-phosphate with dichloromethylenebisphosphonic acid;
monoanhydride of 5-(9-ethylcarbazol-3-ylmethyl)-4-thiouridine-5'-phosphate with dichloromethylenebisphosphonic acid;
monoanhydride of 5-((4-phenyl)phenylthio)-4-thiouridine-5'-phosphate with dichloromethylenebisphosphonic acid;
monoanhydride of 5-(9-methoxyfluoren-9-yl)uridine-5'-phosphate with dichloromethylenebisphosphonic acid;
monoanhydride of 5-((4-phenyl)phenylcarbonyl)uridine-5'-phosphate, monoanhydride with dichloromethylenebisphosphonic acid;
5-diphenylmethyluridine-5'-(tetrahydrogen-triphosphate)-$P^3$-monomethyl ester;
5-diphenylmethyluridine-5'-(tetrahydrogen-triphosphate)-$P^3$-mono(n-propyl)ester;
5-diphenylmethyluridine-5'-(tetrahydrogen-triphosphate)-$P^3$-mono(2-methoxyethyl)ester;
5-diphenylmethyluridine-5'-(tetrahydrogen-triphosphate)-$P^3$-monophenylmethyl ester;
5-diphenylmethyl-4-thiouridine-5'-(tetrahydrogen-triphosphate)-$P^3$-monomethyl ester;
5-(1,1-bis(4-methoxyphenyl)methyl)uridine-5'-(tetrahydrogen-triphosphate)-$P^3$-monomethyl ester;
5-(1,1-bis(4-methoxyphenyl)methyl)-4-thiouridine-5'-(tetrahydrogen triphosphate)-$P^3$-monomethyl ester;
5-(1,1-bis(4-methoxyphenyl)methyl)-4-thiouridine-5'-(dihydrogen-phosphate)-monomethyl ester;
5-(9H-fluoren-9-yl)uridine-5'-(tetrahydrogen-triphosphate)-$P^3$-monomethyl ester;
5-(9H-fluoren-9-yl)-4-thiouridine-5'-(tetrahydrogen-triphosphate)-$P^3$-monomethyl ester;
5-(9H-fluoren-9-yl)-4-thiouridine-5'-(trihydrogen-diphosphate)-$P^3$-monomethyl ester;
5-(9H-fluoren-9-yl)-4-thiouridine-5'-(tetrahydrogen-triphosphate)-$P^3$-monomethyl ester;
5-triphenylsilyluridine-5'-(tetrahydrogen-triphosphate)-$P^3$-monomethyl ester;
5-phenylthiouridine-5'-(tetrahydrogen-triphosphate)-$P^3$-monomethyl ester;

5-ethyl-4-thiouridine-5'-(tetrahydrogen-triphosphate)-P³-monomethyl ester;

5-((4-methoxy)phenylthio)uridine-5'-(tetrahydrogen triphosphate)-P³-monomethyl ester;

5-((2-phenyl)phenylthio)uridine-5'-(tetrahydrogen-triphosphate)-P³-monomethyl ester;

5-((3-phenyl)phenylthio)uridine-5'-(tetrahydrogen-triphosphate)-P³-monomethyl ester;

5-((4-phenyl)phenylthio)uridine-5'-(tetrahydrogen-triphosphate)-P³-monomethyl ester;

5-((2-naphthylthio)uridine-5'-(tetrahydrogen-triphosphate)-P³-monomethyl ester;

5-((3-phenoxy)phenylmethyl)-4-thiouridine-5'-(tetrahydrogen-triphosphate)-P³-monomethyl ester;

5-((4-phenoxy)phenylmethyl)-4-thiouridine-5'-(tetrahydrogen-triphosphate)-P³-monomethyl ester;

5-((3-phenylmethoxy)phenylmethyl)-4-thiouridine-5'-(tetrahydrogen-triphosphate)-P³-monomethyl ester;

5-((4-phenylmethoxy)phenylmethyl)-4-thiouridine-5'-(tetrahydrogen-triphosphate)-P³-monomethyl ester;

5-(4-(1,1-dimethylethyl)phenylmethyl)-4-thiouridine-5'-(tetrahydrogen-triphosphate)-P³-monomethyl ester;

5-(4-(1,1-dimethylethyl)phenylmethyl)-4-thiouridine-5'-(dihydrogen-phosphate)-monomethyl ester;

5-((3-methoxy-4-phenylmethoxy)phenylmethyl)-4-thiouridine-5-(tetrahydrogen-triphosphate)-P³-monomethyl ester; or 5-((3-methoxy-4-phenylmethoxy)phenylmethyl)-4-thiouridine-5'-(trihydrogen-diphosphate)-P²-monomethyl ester;

or pharmaceutically acceptable salts thereof.

8. A process for preparing a compound according to claim 1 which comprises:

(a) for a compound of formula (I) wherein X represents H, deprotecting a compound of formula

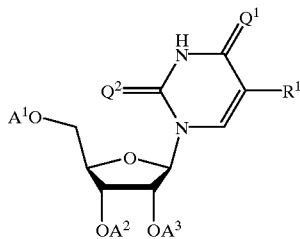

(II)

wherein A¹, A² and A³ each independently represent a protecting group;

(b) for a compound of formula (I) wherein X represents

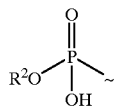

reacting the product of step (a) with a phosphorylating agent P(O)L₃ wherein each L is the same or different and represents a leaving group, to yield an intermediate of formula

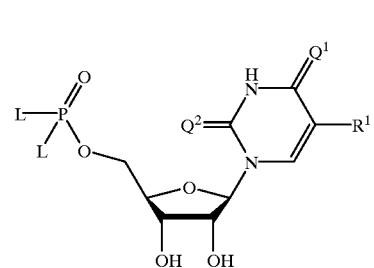

(III)

wherein L is as defined above, and either hydrolysing the intermediate of formula (III) thus obtained under alkaline conditions or reacting it with MeOH followed by alkaline hydrolysis;

(c) for a compound of formula (I) wherein X represents

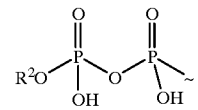

hydrolysing an intermediate of formula (III) as defined above and then reacting it with a phosphorylating agent P(O)L₃ as defined above, and either hydrolysing the product under alkaline conditions or reacting it with MeOH followed by alkaline hydrolysis;

(d) for a compound of formula (I) wherein X represents

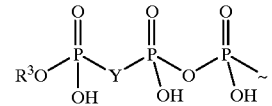

wherein R³ represents H, reacting an intermediate of formula (III) as defined above with a salt of a compound of formula

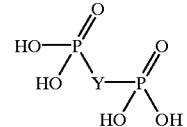

(IV)

followed by alkaline hydrolysis; or (e) for a compound of formula (I) wherein X represents

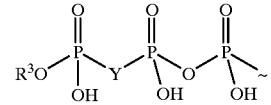

wherein R³ does not represent H, reacting the product of step (d) with a phosphorylating agent P(O)L₃ as defined above, and reacting the product with R³OH wherein R³ is as defined above; and, optionally thereafter any of the above processes forming a salt.

9. A pharmaceutical composition which comprises a compound according to claim 1 in association with a pharmaceutically acceptable excipient or adjuvant.

10. A method of treating a patient suffering from an inflammatory condition which comprises administering to said patient a therapeutically effective amount of a compound according to claim 1.

11. An intermediate of formula (II):

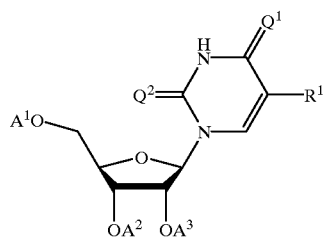

(II)

wherein $A^1$, $A^2$ and $A^3$ each independently represent a protecting group and $Q^1$, $Q^2$, $R^1$ and $R^5$ are as defined in claim 1 provided that $R^1$ does not represent $C_{1-6}$-alkyl or $C(O)R^6$, $CHR^5R^6$ or $SR^6$ when $R^6$ represents unsubstituted phenyl and $R^5$ does not represent a H atom.

12. A method according to claim 10, wherein the inflammatory condition is asthma.

* * * * *